(12) United States Patent
Ballakur et al.

(10) Patent No.: US 10,603,066 B2
(45) Date of Patent: Mar. 31, 2020

(54) FLUID-JET DISSECTION SYSTEM AND METHOD FOR REDUCING THE APPEARANCE OF CELLULITE

(71) Applicant: Ulthera, Inc., Mesa, AZ (US)

(72) Inventors: Sowmya Ballakur, Menlo Park, CA (US); Robert L. Clark, III, Hayward, CA (US); James E. Chomas, Boulder, CO (US); Ben F. Brian, III, Menlo Park, CA (US); David M. Clapper, Atherton, CA (US)

(73) Assignee: ULTHERA, INC., Mesa, AZ (US)

( * ) Notice: Subject to any disclaimer, the term of this patent is extended or adjusted under 35 U.S.C. 154(b) by 345 days.

(21) Appl. No.: 15/151,370

(22) Filed: May 10, 2016

(65) Prior Publication Data

US 2016/0249946 A1 Sep. 1, 2016

Related U.S. Application Data

(63) Continuation of application No. 12/787,377, filed on May 25, 2010, now Pat. No. 9,358,033.

(51) Int. Cl.
*A61B 17/3203* (2006.01)
*A61B 17/00* (2006.01)
(Continued)

(52) U.S. Cl.
CPC .... *A61B 17/3203* (2013.01); *A61B 17/00234* (2013.01); *A61B 18/20* (2013.01);
(Continued)

(58) Field of Classification Search
CPC ........ A61B 2017/306; A61B 17/00234; A61B 17/3203
See application file for complete search history.

(56) References Cited

U.S. PATENT DOCUMENTS 2,370,529 A   2/1945   Fuller
2,490,409 A   12/1949  Brown
(Continued)

FOREIGN PATENT DOCUMENTS

CA   1232837   2/1988
CA   1239092   7/1988
(Continued)

OTHER PUBLICATIONS

Green, Jeremy B. et al. Therapeutic approaches to cellulite. Seminars in Cutaneous Medicine and Surgery, vol. 34, Sep. 2015, pp. 140-143.
(Continued)

*Primary Examiner* — Bhisma Mehta
*Assistant Examiner* — Matthew A Engel
(74) *Attorney, Agent, or Firm* — Knobbe, Martens, Olson & Bear LLP

(57) ABSTRACT

A minimally invasive skin treatment system includes a platform having a recessed area on its bottom and one or more injection ports orthogonal to its top, each injection port including a through-hole to the recessed area. The system includes an injection device including a needle slidably disposed in a selective port such that the needle passes into the recessed area and percutaneously through a dermis disposed within the recessed area. A nozzle is configured to discharge a fluid at a high pressure in a direction orthogonal to an axis of the needle and parallel to the top of the platform to cut create a plane of dissection within the subcutaneous tissue.

11 Claims, 6 Drawing Sheets

(51) Int. Cl.
   *A61B 18/20* (2006.01)
   *A61B 17/30* (2006.01)
   *A61B 18/00* (2006.01)
   *A61M 5/30* (2006.01)
   *A61N 7/00* (2006.01)
   *A61M 5/28* (2006.01)

(52) U.S. Cl.
   CPC ............. *A61B 2017/00747* (2013.01); *A61B 2017/306* (2013.01); *A61B 2017/32035* (2013.01); *A61B 2018/00452* (2013.01); *A61B 2217/005* (2013.01); *A61M 5/28* (2013.01); *A61M 5/3007* (2013.01); *A61N 2007/0008* (2013.01)

(56) References Cited

U.S. PATENT DOCUMENTS

| | | | |
|---|---|---|---|
| 2,738,172 | A | 3/1956 | Spiess et al. |
| 2,945,496 | A | 7/1960 | Fosdal |
| 2,961,382 | A | 11/1960 | Singher et al. |
| 3,129,944 | A | 4/1964 | Amos et al. |
| 3,324,854 | A | 6/1967 | Weese |
| 3,590,808 | A | 7/1971 | Muller |
| 3,735,336 | A | 5/1973 | Long |
| 3,964,482 | A * | 6/1976 | Gerstel ................ A61K 9/0021 424/449 |
| 3,991,763 | A | 11/1976 | Genese |
| 4,150,669 | A | 4/1979 | Latorre |
| 4,188,952 | A | 2/1980 | Loschilov et al. |
| 4,211,949 | A | 7/1980 | Brisken et al. |
| 4,212,206 | A | 7/1980 | Hartemann et al. |
| 4,231,368 | A | 11/1980 | Becker et al. |
| 4,248,231 | A | 2/1981 | Herczog et al. |
| 4,249,923 | A | 2/1981 | Walda |
| 4,276,885 | A | 7/1981 | Tickner et al. |
| 4,299,219 | A | 11/1981 | Norris, Jr. |
| 4,309,989 | A | 1/1982 | Fahim |
| 4,373,458 | A * | 2/1983 | Dorosz ................ D05B 51/00 112/470.06 |
| 4,382,441 | A | 5/1983 | Svedman |
| 4,466,442 | A | 8/1984 | Hilmann et al. |
| 4,497,325 | A | 2/1985 | Wedel |
| 4,536,180 | A | 8/1985 | Johnson |
| 4,549,533 | A | 10/1985 | Cain |
| 4,608,043 | A | 8/1986 | Larkin |
| 4,641,652 | A | 2/1987 | Hutterer et al. |
| 4,646,754 | A | 3/1987 | Seale |
| 4,657,756 | A | 4/1987 | Rasor et al. |
| 4,673,387 | A | 6/1987 | Phillips et al. |
| 4,681,119 | A | 7/1987 | Rasor et al. |
| 4,684,479 | A | 8/1987 | D'Arrigo |
| 4,688,570 | A | 8/1987 | Kramer et al. |
| 4,689,986 | A | 9/1987 | Carson et al. |
| 4,718,433 | A | 1/1988 | Feinstein |
| 4,720,075 | A | 1/1988 | Peterson et al. |
| 4,751,921 | A | 6/1988 | Park |
| 4,762,915 | A | 8/1988 | Kung et al. |
| 4,774,958 | A | 10/1988 | Feinstein |
| 4,796,624 | A | 1/1989 | Trott et al. |
| 4,797,285 | A | 1/1989 | Barenholz et al. |
| 4,815,462 | A | 3/1989 | Clark |
| 4,844,080 | A | 7/1989 | Frass et al. |
| 4,844,470 | A | 7/1989 | Hammon et al. |
| 4,844,882 | A | 7/1989 | Widder et al. |
| 4,886,491 | A | 12/1989 | Parisi et al. |
| 4,900,311 | A | 2/1990 | Stern et al. |
| 4,900,540 | A | 2/1990 | Ryan et al. |
| 4,919,986 | A | 4/1990 | Lay et al. |
| 4,920,954 | A | 5/1990 | Alliger et al. |
| 4,936,281 | A | 6/1990 | Stasz |
| 4,936,303 | A | 6/1990 | Detwiler et al. |
| 4,957,656 | A | 9/1990 | Cerny et al. |
| 5,000,172 | A | 3/1991 | Ward |
| 5,022,414 | A | 6/1991 | Muller |
| 5,040,537 | A | 8/1991 | Katakura |
| 5,050,537 | A | 9/1991 | Fox |
| 5,069,664 | A | 12/1991 | Guess et al. |
| 5,083,568 | A | 1/1992 | Shimazaki et al. |
| 5,088,499 | A | 2/1992 | Unger |
| 5,100,390 | A | 3/1992 | Lubeck et al. |
| 5,131,600 | A | 7/1992 | Klimpel |
| 5,143,063 | A | 9/1992 | Fellner |
| 5,149,319 | A | 9/1992 | Unger |
| 5,158,071 | A | 10/1992 | Umemura et al. |
| 5,170,604 | A | 12/1992 | Hedly |
| 5,178,433 | A | 1/1993 | Wagner |
| 5,203,785 | A | 4/1993 | Slater |
| 5,209,720 | A | 5/1993 | Unger |
| 5,215,104 | A | 6/1993 | Steinert |
| 5,215,680 | A | 6/1993 | D'Arrigo |
| 5,216,130 | A | 6/1993 | Line et al. |
| 5,219,401 | A | 6/1993 | Cathignol et al. |
| 5,261,922 | A | 11/1993 | Hood |
| 5,308,334 | A * | 5/1994 | Sancoff ............... A61M 5/1408 222/103 |
| 5,310,540 | A | 5/1994 | Giddey et al. |
| 5,312,364 | A | 5/1994 | Jacobs |
| 5,315,998 | A | 5/1994 | Tachibana et al. |
| 5,316,000 | A | 5/1994 | Chapelon et al. |
| 5,320,607 | A * | 6/1994 | Ishibashi .......... A61B 5/150022 604/115 |
| 5,323,642 | A | 6/1994 | Condon |
| 5,342,380 | A | 8/1994 | Hood |
| 5,352,436 | A | 10/1994 | Wheatley et al. |
| 5,354,307 | A | 10/1994 | Porowski |
| 5,380,411 | A | 1/1995 | Schlief |
| 5,383,858 | A | 1/1995 | Reilly et al. |
| 5,385,561 | A * | 1/1995 | Cerny ................ A61B 17/3417 604/111 |
| 5,409,126 | A | 4/1995 | DeMars |
| 5,413,574 | A | 5/1995 | Fugo |
| 5,415,160 | A | 5/1995 | Ortiz et al. |
| 5,417,654 | A | 5/1995 | Kelman |
| 5,419,761 | A | 5/1995 | Narayanan et al. |
| 5,419,777 | A | 5/1995 | Hofling et al. |
| 5,425,580 | A | 6/1995 | Beller |
| 5,437,640 | A | 8/1995 | Schwab |
| 5,441,490 | A | 8/1995 | Svedman |
| 5,449,351 | A * | 9/1995 | Zohmann ........... A61B 17/3401 604/158 |
| 5,457,041 | A | 10/1995 | Ginaven et al. |
| 5,476,368 | A | 12/1995 | Rabenau et al. |
| 5,478,315 | A | 12/1995 | Brothers |
| 5,494,038 | A | 2/1996 | Wang et al. |
| 5,507,790 | A | 4/1996 | Weiss |
| 5,522,797 | A | 6/1996 | Grimm |
| 5,533,981 | A | 7/1996 | Mandro et al. |
| 5,545,123 | A | 8/1996 | Ortiz et al. |
| 5,556,406 | A | 9/1996 | Gordon et al. |
| 5,562,693 | A | 10/1996 | Devlin et al. |
| 5,569,242 | A | 10/1996 | Lax et al. |
| 5,571,131 | A | 11/1996 | Ek et al. |
| 5,573,002 | A | 11/1996 | Pratt |
| 5,573,497 | A | 11/1996 | Chapelon |
| 5,590,657 | A | 1/1997 | Cain |
| 5,601,526 | A | 2/1997 | Chapelon |
| 5,601,584 | A | 2/1997 | Obaji et al. |
| 5,607,441 | A | 3/1997 | Sierocuk et al. |
| 5,634,911 | A | 6/1997 | Hermann et al. |
| 5,639,443 | A | 6/1997 | Schutt et al. |
| 5,649,947 | A | 7/1997 | Auerbach et al. |
| 5,662,646 | A | 9/1997 | Fumich |
| 5,681,026 | A | 10/1997 | Durand |
| 5,690,657 | A | 11/1997 | Koepnick |
| 5,695,460 | A | 12/1997 | Siegel et al. |
| 5,716,326 | A | 2/1998 | Dannan |
| 5,733,572 | A | 3/1998 | Unger et al. |
| 5,755,753 | A | 5/1998 | Knowlton |
| 5,766,198 | A | 6/1998 | Li |
| 5,772,688 | A * | 6/1998 | Muroki ................ A61N 1/24 600/372 |
| 5,778,894 | A | 7/1998 | Dorogi et al. |
| 5,792,140 | A | 8/1998 | Tu |

(56) References Cited

U.S. PATENT DOCUMENTS

| | | |
|---|---|---|
| 5,795,311 A | 8/1998 | Wess |
| 5,797,627 A * | 8/1998 | Salter .................. F16L 31/00 285/239 |
| 5,810,765 A | 9/1998 | Oda |
| 5,817,054 A | 10/1998 | Grimm |
| 5,817,115 A | 10/1998 | Nigam |
| 5,827,204 A | 10/1998 | Grandia et al. |
| 5,827,216 A | 10/1998 | Igo et al. |
| 5,865,309 A | 2/1999 | Futagawa et al. |
| 5,871,524 A | 2/1999 | Knowlton |
| 5,884,631 A | 3/1999 | Silberg |
| 5,885,232 A | 3/1999 | Guitay |
| 5,902,272 A | 5/1999 | Eggers et al. |
| 5,911,700 A | 6/1999 | Mozsary et al. |
| 5,911,703 A * | 6/1999 | Slate .................. A61M 5/30 604/135 |
| 5,918,757 A | 7/1999 | Przytulla et al. |
| 5,919,219 A | 7/1999 | Knowlton |
| 5,935,142 A | 8/1999 | Hood |
| 5,935,143 A | 8/1999 | Hood |
| 5,942,408 A | 8/1999 | Christensen et al. |
| 5,948,011 A | 9/1999 | Knowlton |
| 5,961,475 A | 10/1999 | Guitay |
| 5,964,776 A | 10/1999 | Peyman |
| 5,976,153 A | 11/1999 | Fischell et al. |
| 5,976,163 A | 11/1999 | Nigam |
| 5,980,517 A | 11/1999 | Gough |
| 5,983,131 A * | 11/1999 | Weaver .................. A61N 1/0424 435/173.6 |
| 5,984,915 A | 11/1999 | Loeb et al. |
| 5,993,423 A * | 11/1999 | Choi .................. A61M 5/158 128/DIG. 12 |
| 5,997,501 A * | 12/1999 | Gross .................. A61M 5/14248 604/65 |
| 6,035,897 A | 3/2000 | Kozyuk |
| 6,039,048 A | 3/2000 | Silberg |
| 6,042,539 A | 3/2000 | Harper et al. |
| 6,047,215 A | 4/2000 | McClure et al. |
| 6,048,337 A * | 4/2000 | Svedman .................. A61B 10/0035 604/289 |
| 6,066,131 A * | 5/2000 | Mueller .................. A61B 17/3403 606/15 |
| 6,071,239 A | 6/2000 | Cribbs et al. |
| 6,083,236 A | 7/2000 | Feingold |
| 6,102,887 A | 8/2000 | Altman |
| 6,113,558 A | 9/2000 | Rosenschein et al. |
| 6,117,152 A | 9/2000 | Huitema |
| RE36,939 E | 10/2000 | Tachibana et al. |
| 6,128,958 A | 10/2000 | Cain |
| 6,132,755 A * | 10/2000 | Eicher .................. A61M 31/002 424/427 |
| 6,139,518 A | 10/2000 | Mozary et al. |
| 6,155,989 A | 12/2000 | Collins |
| 6,162,232 A | 12/2000 | Shadduck |
| 6,176,854 B1 | 1/2001 | Cone |
| 6,183,442 B1 | 2/2001 | Athanasiou et al. |
| 6,193,672 B1 | 2/2001 | Clement |
| 6,200,291 B1 | 3/2001 | Di Pietro |
| 6,200,313 B1 | 3/2001 | Abe et al. |
| 6,203,540 B1 | 3/2001 | Weber et al. |
| 6,210,393 B1 | 4/2001 | Brisken |
| 6,214,018 B1 | 4/2001 | Kreizman et al. |
| 6,237,604 B1 | 5/2001 | Burnside et al. |
| 6,241,753 B1 | 6/2001 | Knowlten |
| 6,254,580 B1 | 7/2001 | Svedman |
| 6,254,614 B1 | 7/2001 | Jesseph |
| 6,258,056 B1 | 7/2001 | Turley et al. |
| 6,258,378 B1 | 7/2001 | Schneider et al. |
| 6,261,272 B1 * | 7/2001 | Gross .................. A61M 5/2053 604/272 |
| 6,273,877 B1 * | 8/2001 | West .................. A61B 17/3401 604/264 |
| 6,277,116 B1 * | 8/2001 | Utely .................. A61B 18/14 606/41 |
| 6,280,401 B1 | 8/2001 | Mahurkar |
| 6,287,274 B1 | 9/2001 | Sussman et al. |
| 6,302,863 B1 | 10/2001 | Tankovich |
| 6,309,355 B1 | 10/2001 | Cain et al. |
| 6,311,090 B1 | 10/2001 | Knowlton |
| 6,312,439 B1 | 11/2001 | Gordon |
| 6,315,756 B1 | 11/2001 | Tankovich |
| 6,315,777 B1 | 11/2001 | Comben |
| 6,319,230 B1 | 11/2001 | Palasis et al. |
| 6,321,109 B2 | 11/2001 | Ben-Haim et al. |
| 6,325,801 B1 | 12/2001 | Monnier |
| 6,338,710 B1 | 1/2002 | Takahashi et al. |
| 6,350,276 B1 | 2/2002 | Knowlton |
| 6,366,206 B1 | 4/2002 | Ishikawa |
| 6,375,634 B1 | 4/2002 | Carroll |
| 6,377,854 B1 | 4/2002 | Knowlton |
| 6,377,855 B1 | 4/2002 | Knowlton |
| 6,381,497 B1 | 4/2002 | Knowlton |
| 6,381,498 B1 | 4/2002 | Knowlton |
| 6,387,380 B1 | 5/2002 | Knowlton |
| 6,391,020 B1 | 5/2002 | Kurtz et al. |
| 6,391,023 B1 | 5/2002 | Weber et al. |
| 6,397,098 B1 | 5/2002 | Uber, III et al. |
| 6,405,090 B1 | 6/2002 | Knowlton |
| 6,409,665 B1 | 6/2002 | Scott et al. |
| 6,413,216 B1 | 7/2002 | Cain et al. |
| 6,413,255 B1 | 7/2002 | Stern |
| 6,425,912 B1 | 7/2002 | Knowlton |
| 6,430,446 B1 | 8/2002 | Knowlton |
| 6,432,101 B1 | 8/2002 | Weber et al. |
| 6,436,078 B1 | 8/2002 | Svedman |
| 6,438,424 B1 | 8/2002 | Knowlton |
| 6,440,096 B1 * | 8/2002 | Lastovich .................. A61B 17/205 424/448 |
| 6,440,121 B1 | 8/2002 | Weber et al. |
| 6,443,914 B1 | 9/2002 | Costantino |
| 6,450,979 B1 | 9/2002 | Miwa |
| 6,451,240 B1 * | 9/2002 | Sherman .................. A61M 37/0015 205/164 |
| 6,453,202 B1 | 9/2002 | Knowlton |
| 6,454,730 B1 | 9/2002 | Hechel et al. |
| 6,461,350 B1 | 10/2002 | Underwood et al. |
| 6,461,378 B1 | 10/2002 | Knowlton |
| 6,464,680 B1 | 10/2002 | Brisken et al. |
| 6,470,216 B1 | 10/2002 | Knowlton |
| 6,470,218 B1 | 10/2002 | Behl |
| 6,479,034 B1 | 11/2002 | Unger et al. |
| 6,500,141 B1 * | 12/2002 | Irion .................. A61N 7/00 601/2 |
| 6,506,611 B2 | 1/2003 | Bienert et al. |
| 6,511,463 B1 * | 1/2003 | Wood .................. A61M 37/0015 216/75 |
| 6,514,220 B2 | 2/2003 | Melton |
| 6,517,498 B1 * | 2/2003 | Burbank .................. A61B 10/0233 600/564 |
| 6,537,242 B1 | 3/2003 | Palmer |
| 6,537,246 B1 | 3/2003 | Unger et al. |
| 6,544,201 B1 | 4/2003 | Guitay |
| 6,569,176 B2 | 5/2003 | Jesseph |
| 6,572,839 B2 | 6/2003 | Sugita |
| 6,575,930 B1 | 6/2003 | Trombley, III et al. |
| 6,582,442 B2 | 6/2003 | Simon et al. |
| 6,585,678 B1 | 7/2003 | Tachibana et al. |
| 6,599,305 B1 | 7/2003 | Feingold |
| 6,602,251 B2 | 8/2003 | Burbank et al. |
| 6,605,079 B2 | 8/2003 | Shanks et al. |
| 6,605,080 B1 | 8/2003 | Altshuler et al. |
| 6,607,498 B2 | 8/2003 | Eshel |
| 6,611,707 B1 * | 8/2003 | Prausnitz .................. A61B 5/14514 604/21 |
| 6,615,166 B1 | 9/2003 | Guheen et al. |
| 6,623,457 B1 * | 9/2003 | Rosenberg .................. A61B 17/205 604/191 |
| 6,626,854 B2 | 9/2003 | Friedman et al. |
| 6,629,949 B1 * | 10/2003 | Douglas .................. A61M 5/142 604/19 |
| 6,638,767 B2 | 10/2003 | Unger et al. |
| 6,645,162 B2 | 11/2003 | Friedman et al. |

(56) References Cited

U.S. PATENT DOCUMENTS

| | | | |
|---|---|---|---|
| 6,662,054 B2 | 12/2003 | Kreindel et al. | |
| 6,663,616 B1 | 12/2003 | Roth et al. | |
| 6,663,618 B2 | 12/2003 | Weber et al. | |
| 6,663,820 B2* | 12/2003 | Arias | A61M 37/0015 |
| | | | 264/225 |
| 6,685,657 B2 | 2/2004 | Jones | |
| 6,687,537 B2 | 2/2004 | Bernabei | |
| 6,695,781 B2 | 2/2004 | Rabiner | |
| 6,695,808 B2 | 2/2004 | Tom | |
| 6,702,779 B2* | 3/2004 | Connelly | A61M 5/14248 |
| | | | 604/890.1 |
| 6,725,095 B2 | 4/2004 | Fenn et al. | |
| 6,730,061 B1 | 5/2004 | Cuschieri et al. | |
| 6,743,211 B1 | 6/2004 | Prausnitz et al. | |
| 6,743,214 B2 | 6/2004 | Heil et al. | |
| 6,743,215 B2 | 6/2004 | Bernabei | |
| 6,749,624 B2 | 6/2004 | Knowlton | |
| 6,770,071 B2 | 8/2004 | Woloszko et al. | |
| 6,780,171 B2* | 8/2004 | Gabel | A61M 5/14248 |
| | | | 604/181 |
| 6,795,727 B2 | 9/2004 | Giammarusti | |
| 6,795,728 B2 | 9/2004 | Chornenky et al. | |
| 6,817,988 B2 | 11/2004 | Bergeron et al. | |
| 6,826,429 B2 | 11/2004 | Johnson et al. | |
| 6,855,133 B2 | 2/2005 | Svedman | |
| 6,882,884 B1 | 4/2005 | Mosk et al. | |
| 6,883,729 B2 | 4/2005 | Putvinski et al. | |
| 6,889,090 B2 | 5/2005 | Kreindel | |
| 6,892,099 B2 | 5/2005 | Jaafar et al. | |
| 6,896,659 B2 | 5/2005 | Conston et al. | |
| 6,896,666 B2 | 5/2005 | Kochamba | |
| 6,896,674 B1 | 5/2005 | Woloszko et al. | |
| 6,902,554 B2* | 6/2005 | Huttner | A61B 17/00 |
| | | | 604/116 |
| 6,905,480 B2 | 6/2005 | McGuckin et al. | |
| 6,910,671 B1 | 6/2005 | Korkus et al. | |
| 6,916,328 B2 | 7/2005 | Brett et al. | |
| 6,918,907 B2* | 7/2005 | Kelly | A61B 18/1477 |
| | | | 606/100 |
| 6,918,908 B2 | 7/2005 | Bonner et al. | |
| 6,920,883 B2 | 7/2005 | Bessette et al. | |
| 6,926,683 B1 | 8/2005 | Kochman et al. | |
| 6,931,277 B1 | 8/2005 | Yuzhakov et al. | |
| 6,945,937 B2 | 9/2005 | Culp et al. | |
| 6,957,186 B1 | 10/2005 | Guheen et al. | |
| 6,960,205 B2 | 11/2005 | Jahns et al. | |
| 6,971,994 B1 | 12/2005 | Young | |
| 6,974,450 B2 | 12/2005 | Weber | |
| 6,994,691 B2 | 2/2006 | Ejlerson | |
| 6,994,705 B2 | 2/2006 | Nebis et al. | |
| 7,066,922 B2 | 6/2006 | Angel et al. | |
| 7,083,580 B2 | 8/2006 | Bernabei | |
| 7,115,108 B2* | 10/2006 | Wilkinson | A61M 5/14248 |
| | | | 604/93.01 |
| 7,149,698 B2 | 12/2006 | Guheen et al. | |
| 7,153,306 B2 | 12/2006 | Ralph et al. | |
| 7,169,115 B2 | 1/2007 | Nobis et al. | |
| 7,184,614 B2 | 2/2007 | Slatkine | |
| 7,184,826 B2* | 2/2007 | Cormier | A61M 37/0015 |
| | | | 604/20 |
| 7,186,252 B2 | 3/2007 | Nobis et al. | |
| 7,217,265 B2 | 5/2007 | Hennings | |
| 7,223,275 B2 | 5/2007 | Shiuey | |
| 7,226,446 B1 | 6/2007 | Mody et al. | |
| 7,238,183 B2 | 7/2007 | Kreindel | |
| 7,250,047 B2 | 7/2007 | Anderson et al. | |
| 7,252,641 B2 | 8/2007 | Thompson et al. | |
| 7,258,674 B2 | 8/2007 | Cribbs et al. | |
| 7,278,991 B2 | 10/2007 | Morris et al. | |
| 7,306,095 B1 | 12/2007 | Bourque et al. | |
| 7,315,826 B1 | 1/2008 | Guheen et al. | |
| 7,331,951 B2 | 2/2008 | Eschel et al. | |
| 7,335,158 B2 | 2/2008 | Taylor | |
| 7,338,551 B2 | 3/2008 | Kozyuk | |
| 7,347,855 B2 | 3/2008 | Eshel et al. | |
| 7,351,295 B2 | 4/2008 | Pawlik et al. | |
| 7,374,551 B2 | 5/2008 | Liang | |
| 7,376,460 B2 | 5/2008 | Bernabei | |
| 7,392,080 B2* | 6/2008 | Eppstein | A61M 37/0015 |
| | | | 604/20 |
| 7,410,476 B2 | 8/2008 | Wilkinson et al. | |
| 7,419,798 B2 | 9/2008 | Ericson | |
| 7,437,189 B2* | 10/2008 | Matsumura | A61N 1/306 |
| | | | 604/21 |
| 7,442,192 B2 | 10/2008 | Knowlton | |
| 7,452,358 B2 | 11/2008 | Stern et al. | |
| 7,455,663 B2* | 11/2008 | Bikovsky | A61M 5/1413 |
| | | | 604/240 |
| 7,470,237 B2 | 12/2008 | Beckman et al. | |
| 7,473,251 B2 | 1/2009 | Knowlton et al. | |
| 7,479,104 B2* | 1/2009 | Lau | A61B 17/0206 |
| | | | 600/37 |
| 7,494,488 B2 | 2/2009 | Weber | |
| 7,507,209 B2 | 3/2009 | Nezhat | |
| 7,524,318 B2 | 4/2009 | Young et al. | |
| 7,546,918 B2 | 6/2009 | Gollier et al. | |
| 7,559,905 B2 | 7/2009 | Kagosaki et al. | |
| 7,566,318 B2 | 7/2009 | Haefner | |
| 7,585,281 B2 | 9/2009 | Nezhat et al. | |
| 7,588,547 B2 | 9/2009 | Deem et al. | |
| 7,588,557 B2 | 9/2009 | Nakao | |
| 7,601,128 B2 | 10/2009 | Deem et al. | |
| 7,625,354 B2 | 12/2009 | Hochman | |
| 7,625,371 B2 | 12/2009 | Morris et al. | |
| 7,678,097 B1 | 3/2010 | Peluso et al. | |
| 7,740,600 B2 | 6/2010 | Slatkine et al. | |
| 7,762,964 B2 | 7/2010 | Slatkine et al. | |
| 7,762,965 B2 | 7/2010 | Slatkine et al. | |
| 7,770,611 B2 | 8/2010 | Houwaert et al. | |
| 7,771,374 B2 | 8/2010 | Slatkine et al. | |
| 7,824,348 B2 | 11/2010 | Barthe et al. | |
| 7,828,827 B2* | 11/2010 | Gartstein | A45D 26/0004 |
| | | | 606/290 |
| 7,842,008 B2 | 11/2010 | Clarke et al. | |
| 7,901,421 B2 | 3/2011 | Shiuey et al. | |
| 7,935,139 B2 | 5/2011 | Slatkine et al. | |
| 7,938,824 B2 | 5/2011 | Chornenky et al. | |
| 7,967,763 B2 | 6/2011 | Deem et al. | |
| 7,985,199 B2* | 7/2011 | Kornerup | A61M 5/158 |
| | | | 604/93.01 |
| 7,988,667 B2 | 8/2011 | Imai | |
| 8,025,658 B2* | 9/2011 | Chong | A61M 5/1413 |
| | | | 604/890.1 |
| 8,083,715 B2 | 12/2011 | Sonoda et al. | |
| 8,086,322 B2* | 12/2011 | Schouenborg | A61N 1/0456 |
| | | | 600/372 |
| 8,103,355 B2 | 1/2012 | Mulholland et al. | |
| 8,127,771 B2 | 3/2012 | Hennings | |
| 8,133,191 B2 | 3/2012 | Rosenberg et al. | |
| 8,256,429 B2 | 9/2012 | Hennings et al. | |
| 8,348,867 B2 | 1/2013 | Deem et al. | |
| 8,357,146 B2 | 1/2013 | Hennings et al. | |
| 8,366,643 B2 | 2/2013 | Deem et al. | |
| 8,401,668 B2* | 3/2013 | Deem | A61B 18/18 |
| | | | 607/101 |
| 8,406,894 B2 | 3/2013 | Johnson et al. | |
| 8,439,940 B2 | 5/2013 | Chomas et al. | |
| 8,518,069 B2 | 8/2013 | Clark, III et al. | |
| 8,535,302 B2 | 9/2013 | Ben-Haim et al. | |
| 8,540,705 B2 | 9/2013 | Mehta | |
| 8,573,227 B2 | 11/2013 | Hennings et al. | |
| 8,608,737 B2 | 12/2013 | Mehta et al. | |
| 8,636,665 B2 | 1/2014 | Slayton et al. | |
| 8,652,123 B2 | 2/2014 | Gurtner et al. | |
| 8,663,112 B2 | 3/2014 | Slayton et al. | |
| 8,671,622 B2 | 3/2014 | Thomas | |
| 8,672,848 B2 | 3/2014 | Slayton et al. | |
| 8,676,338 B2 | 3/2014 | Levinson | |
| 8,685,012 B2 | 4/2014 | Hennings et al. | |
| 8,753,339 B2* | 6/2014 | Clark, III | A61B 18/1477 |
| | | | 606/45 |
| 8,758,366 B2 | 6/2014 | McLean et al. | |

(56) References Cited

U.S. PATENT DOCUMENTS

| | | |
|---|---|---|
| 8,771,263 B2 | 7/2014 | Epshtein et al. |
| 8,825,176 B2 | 9/2014 | Johnson et al. |
| 8,834,547 B2 | 9/2014 | Anderson et al. |
| 8,868,204 B2 | 10/2014 | Edoute et al. |
| 8,882,753 B2 | 11/2014 | Mehta et al. |
| 8,882,758 B2 | 11/2014 | Nebrigie et al. |
| 8,894,678 B2 | 11/2014 | Clark, III et al. |
| 8,900,261 B2 | 12/2014 | Clark, III et al. |
| 8,900,262 B2 | 12/2014 | Clark, III et al. |
| 8,979,882 B2 | 3/2015 | Drews et al. |
| 9,011,473 B2 | 4/2015 | Clark, III et al. |
| 9,039,722 B2 | 5/2015 | Clark, III et al. |
| 9,345,456 B2 | 5/2016 | Tsonton et al. |
| 9,358,033 B2 * | 6/2016 | Ballakur ............... A61B 17/3203 |
| 9,364,246 B2 | 6/2016 | Clark, III et al. |
| 2001/0001829 A1 | 5/2001 | Sugimura et al. |
| 2001/0004702 A1 | 6/2001 | Peyman |
| 2001/0014805 A1 | 8/2001 | Burbank et al. |
| 2001/0053887 A1 | 12/2001 | Douglas et al. |
| 2002/0029053 A1 | 3/2002 | Gordon |
| 2002/0082528 A1 | 6/2002 | Friedman et al. |
| 2002/0082589 A1 | 6/2002 | Friedman et al. |
| 2002/0099356 A1 | 7/2002 | Unger et al. |
| 2002/0111569 A1 | 8/2002 | Rosenschein |
| 2002/0120238 A1 | 8/2002 | McGuckin et al. |
| 2002/0120260 A1 * | 8/2002 | Morris ............... A61B 18/1477 606/41 |
| 2002/0120261 A1 | 8/2002 | Morris et al. |
| 2002/0130126 A1 | 9/2002 | Rosenberg |
| 2002/0134733 A1 | 9/2002 | Kerfoot |
| 2002/0137991 A1 | 9/2002 | Scarantino |
| 2002/0143326 A1 | 10/2002 | Foley et al. |
| 2002/0169394 A1 * | 11/2002 | Eppstein ............... A61B 5/00 600/573 |
| 2002/0177846 A1 | 11/2002 | Muller |
| 2002/0185557 A1 | 12/2002 | Sparks |
| 2002/0193784 A1 | 12/2002 | McHale et al. |
| 2002/0193831 A1 | 12/2002 | Smith, III |
| 2003/0006677 A1 | 1/2003 | Okuda et al. |
| 2003/0009153 A1 | 1/2003 | Brisken et al. |
| 2003/0069502 A1 | 4/2003 | Makin et al. |
| 2003/0074023 A1 | 4/2003 | Kaplan et al. |
| 2003/0083536 A1 | 5/2003 | Eshel et al. |
| 2003/0120269 A1 | 6/2003 | Bessette et al. |
| 2003/0130628 A1 | 7/2003 | Duffy |
| 2003/0130655 A1 | 7/2003 | Woloszko et al. |
| 2003/0130711 A1 | 7/2003 | Pearson et al. |
| 2003/0139740 A1 | 7/2003 | Kreindel |
| 2003/0139755 A1 | 7/2003 | Dybbs |
| 2003/0153905 A1 | 8/2003 | Edwards et al. |
| 2003/0153960 A1 | 8/2003 | Chornenky et al. |
| 2003/0158566 A1 | 8/2003 | Brett |
| 2003/0171670 A1 | 9/2003 | Gumb et al. |
| 2003/0187371 A1 | 10/2003 | Vortman et al. |
| 2003/0212350 A1 | 11/2003 | Tadlock |
| 2003/0228254 A1 | 12/2003 | Klaveness et al. |
| 2003/0233083 A1 | 12/2003 | Houwaert |
| 2003/0233110 A1 | 12/2003 | Jesseph |
| 2004/0006566 A1 | 1/2004 | Taylor et al. |
| 2004/0019299 A1 | 1/2004 | Ritchart et al. |
| 2004/0019371 A1 | 1/2004 | Jaafar et al. |
| 2004/0023844 A1 | 2/2004 | Pettis et al. |
| 2004/0030263 A1 | 2/2004 | Dubrul et al. |
| 2004/0039312 A1 | 2/2004 | Hillstead et al. |
| 2004/0058882 A1 | 3/2004 | Eriksson et al. |
| 2004/0073144 A1 | 4/2004 | Carava |
| 2004/0073206 A1 | 4/2004 | Foley et al. |
| 2004/0079371 A1 | 4/2004 | Gray |
| 2004/0097967 A1 | 5/2004 | Ignon |
| 2004/0106867 A1 | 6/2004 | Eshel et al. |
| 2004/0120861 A1 | 6/2004 | Petroff |
| 2004/0122483 A1 | 6/2004 | Nathan et al. |
| 2004/0138712 A1 | 7/2004 | Tamarkin et al. |
| 2004/0158150 A1 | 8/2004 | Rabiner |
| 2004/0162546 A1 | 8/2004 | Liang et al. |
| 2004/0162554 A1 | 8/2004 | Lee et al. |
| 2004/0167558 A1 | 8/2004 | Igo et al. |
| 2004/0186425 A1 | 9/2004 | Schneider et al. |
| 2004/0200909 A1 | 10/2004 | McMillan et al. |
| 2004/0202576 A1 * | 10/2004 | Aceti ............... A61B 5/14532 422/82.05 |
| 2004/0206365 A1 | 10/2004 | Knowlton |
| 2004/0210214 A1 | 10/2004 | Knowlton |
| 2004/0215101 A1 | 10/2004 | Rioux et al. |
| 2004/0215110 A1 | 10/2004 | Kreindel |
| 2004/0220512 A1 | 11/2004 | Kreindel |
| 2004/0236248 A1 | 11/2004 | Svedman |
| 2004/0236252 A1 | 11/2004 | Muzzi et al. |
| 2004/0243159 A1 | 12/2004 | Shiuey |
| 2004/0243160 A1 | 12/2004 | Shiuey et al. |
| 2004/0251566 A1 | 12/2004 | Kozyuk |
| 2004/0253148 A1 | 12/2004 | Leaton |
| 2004/0253183 A1 | 12/2004 | Uber, III et al. |
| 2004/0264293 A1 | 12/2004 | Lauharn et al. |
| 2005/0010197 A1 * | 1/2005 | Lau ............... A61B 17/0206 606/1 |
| 2005/0015024 A1 | 1/2005 | Babaev |
| 2005/0027242 A1 * | 2/2005 | Gabel ............... A61M 5/14248 604/93.01 |
| 2005/0033338 A1 | 2/2005 | Ferree |
| 2005/0049543 A1 | 3/2005 | Anderson et al. |
| 2005/0055018 A1 | 3/2005 | Kreindel |
| 2005/0080333 A1 | 4/2005 | Piron et al. |
| 2005/0085748 A1 | 4/2005 | Culp et al. |
| 2005/0102009 A1 | 5/2005 | Costantino |
| 2005/0131439 A1 | 6/2005 | Brett et al. |
| 2005/0136548 A1 | 6/2005 | McDevitt |
| 2005/0137525 A1 | 6/2005 | Wang et al. |
| 2005/0139142 A1 | 6/2005 | Kelley et al. |
| 2005/0154309 A1 | 7/2005 | Etchells et al. |
| 2005/0154314 A1 | 7/2005 | Quistgaard |
| 2005/0154443 A1 | 7/2005 | Linder et al. |
| 2005/0163711 A1 | 7/2005 | Nycz et al. |
| 2005/0182385 A1 | 8/2005 | Epley |
| 2005/0182462 A1 | 8/2005 | Chornenky et al. |
| 2005/0191252 A1 | 9/2005 | Mitsui |
| 2005/0197633 A1 | 9/2005 | Schwartz et al. |
| 2005/0203497 A1 | 9/2005 | Speeg |
| 2005/0215987 A1 | 9/2005 | Slatkine |
| 2005/0234527 A1 | 10/2005 | Slatkine |
| 2005/0256536 A1 | 11/2005 | Grundeman et al. |
| 2005/0268703 A1 | 12/2005 | Funck et al. |
| 2006/0036300 A1 | 2/2006 | Kreindel |
| 2006/0058678 A1 | 3/2006 | Vitek et al. |
| 2006/0074313 A1 | 4/2006 | Slayton |
| 2006/0074314 A1 | 4/2006 | Slayton et al. |
| 2006/0079921 A1 | 4/2006 | Nezhat et al. |
| 2006/0094988 A1 | 5/2006 | Tosaya et al. |
| 2006/0100555 A1 | 5/2006 | Cagle et al. |
| 2006/0102174 A1 | 5/2006 | Hochman |
| 2006/0111744 A1 | 5/2006 | Makin et al. |
| 2006/0122509 A1 | 6/2006 | Desilets |
| 2006/0206040 A1 | 9/2006 | Greenberg |
| 2006/0206117 A1 | 9/2006 | Harp |
| 2006/0211958 A1 | 9/2006 | Rosenberg et al. |
| 2006/0235371 A1 | 10/2006 | Wakamatsu et al. |
| 2006/0235732 A1 | 10/2006 | Miller et al. |
| 2006/0241672 A1 | 10/2006 | Zadini et al. |
| 2006/0241673 A1 | 10/2006 | Zadini |
| 2006/0259102 A1 | 11/2006 | Slatkine |
| 2006/0264809 A1 | 11/2006 | Hansmann et al. |
| 2006/0264926 A1 * | 11/2006 | Kochamba ............. A61M 5/14248 606/41 |
| 2006/0293722 A1 | 12/2006 | Slatkine et al. |
| 2007/0005091 A1 | 1/2007 | Zadini et al. |
| 2007/0010810 A1 | 1/2007 | Kochamba |
| 2007/0016234 A1 | 1/2007 | Daxer |
| 2007/0027411 A1 | 2/2007 | Ella et al. |
| 2007/0031482 A1 | 2/2007 | Castro et al. |
| 2007/0035201 A1 | 2/2007 | Desilets et al. |
| 2007/0041961 A1 | 2/2007 | Hwang et al. |
| 2007/0043295 A1 | 2/2007 | Chomas et al. |
| 2007/0055156 A1 | 3/2007 | Desilets et al. |

(56) References Cited

U.S. PATENT DOCUMENTS

| | | | |
|---|---|---|---|
| 2007/0055179 A1* | 3/2007 | Deem | A61K 41/0028 601/2 |
| 2007/0060989 A1* | 3/2007 | Deem | A61B 18/1477 607/99 |
| 2007/0118077 A1 | 5/2007 | Clarke et al. | |
| 2007/0118166 A1 | 5/2007 | Nobis et al. | |
| 2007/0129708 A1 | 6/2007 | Edwards et al. | |
| 2007/0142881 A1 | 6/2007 | Hennings | |
| 2007/0156096 A1 | 7/2007 | Sonoda et al. | |
| 2007/0179515 A1 | 8/2007 | Matsutani et al. | |
| 2007/0191827 A1 | 8/2007 | Lischinsky et al. | |
| 2007/0197907 A1 | 8/2007 | Bruder et al. | |
| 2007/0197917 A1 | 8/2007 | Bagge | |
| 2007/0239075 A1 | 10/2007 | Manstein et al. | |
| 2007/0239079 A1 | 10/2007 | Manstein et al. | |
| 2007/0255355 A1 | 11/2007 | Altshuler et al. | |
| 2007/0270745 A1 | 11/2007 | Nezhat et al. | |
| 2007/0282318 A1 | 12/2007 | Spooner et al. | |
| 2007/0293849 A1 | 12/2007 | Hennings et al. | |
| 2008/0014627 A1* | 1/2008 | Merchant | A61M 37/0092 435/259 |
| 2008/0015435 A1 | 1/2008 | Cribbs et al. | |
| 2008/0015624 A1 | 1/2008 | Sonoda et al. | |
| 2008/0027328 A1 | 1/2008 | Klopotek et al. | |
| 2008/0027384 A1* | 1/2008 | Wang | A61M 37/0015 604/115 |
| 2008/0058603 A1 | 3/2008 | Edelstein et al. | |
| 2008/0058851 A1 | 3/2008 | Edelstein et al. | |
| 2008/0091126 A1 | 4/2008 | Greenburg | |
| 2008/0091182 A1 | 4/2008 | Mehta | |
| 2008/0109023 A1 | 5/2008 | Greer | |
| 2008/0147084 A1 | 6/2008 | Bleich et al. | |
| 2008/0172012 A1 | 7/2008 | Hiniduma-Lokuge et al. | |
| 2008/0183164 A1 | 7/2008 | Elkins et al. | |
| 2008/0188835 A1 | 8/2008 | Hennings et al. | |
| 2008/0195036 A1* | 8/2008 | Merchant | A61N 7/00 604/24 |
| 2008/0200845 A1 | 8/2008 | Sokka et al. | |
| 2008/0200864 A1* | 8/2008 | Holzbaur | A61N 7/00 604/24 |
| 2008/0215039 A1 | 9/2008 | Slatkine et al. | |
| 2008/0234609 A1 | 9/2008 | Kreindel et al. | |
| 2008/0249526 A1 | 10/2008 | Knowlton | |
| 2008/0262527 A1 | 10/2008 | Eder et al. | |
| 2008/0269668 A1 | 10/2008 | Keenan et al. | |
| 2008/0269687 A1* | 10/2008 | Chong | A61L 15/58 604/180 |
| 2008/0306476 A1 | 12/2008 | Hennings et al. | |
| 2008/0319356 A1 | 12/2008 | Cain et al. | |
| 2008/0319358 A1 | 12/2008 | Lai | |
| 2009/0012434 A1 | 1/2009 | Anderson | |
| 2009/0018522 A1 | 1/2009 | Weintraub et al. | |
| 2009/0024192 A1 | 1/2009 | Mulholland | |
| 2009/0048544 A1 | 2/2009 | Rybyanets | |
| 2009/0088823 A1 | 4/2009 | Barak et al. | |
| 2009/0093864 A1 | 4/2009 | Anderson | |
| 2009/0118722 A1 | 5/2009 | Ebbers et al. | |
| 2009/0124973 A1* | 5/2009 | D'Agostino | A61F 9/0017 604/117 |
| 2009/0125013 A1 | 5/2009 | Sypniewski et al. | |
| 2009/0156958 A1 | 6/2009 | Mehta et al. | |
| 2009/0171255 A1 | 7/2009 | Rybyanets et al. | |
| 2009/0192441 A1 | 7/2009 | Gelbart et al. | |
| 2009/0198189 A1 | 8/2009 | Simons et al. | |
| 2009/0221938 A1 | 9/2009 | Rosenberg et al. | |
| 2009/0240188 A1* | 9/2009 | Hyde | A61M 5/14276 604/20 |
| 2009/0248004 A1 | 10/2009 | Altshuler et al. | |
| 2009/0270789 A1* | 10/2009 | Maxymiv | A61B 17/00234 604/22 |
| 2009/0275879 A1 | 11/2009 | Deem et al. | |
| 2009/0275899 A1 | 11/2009 | Deem et al. | |
| 2009/0275967 A1 | 11/2009 | Stokes et al. | |
| 2009/0326439 A1* | 12/2009 | Chomas | A61B 18/1477 604/21 |
| 2009/0326441 A1* | 12/2009 | Iliescu | A61M 37/0015 604/22 |
| 2009/0326461 A1* | 12/2009 | Gresham | A61B 17/3421 604/164.04 |
| 2010/0004536 A1 | 1/2010 | Rosenberg | |
| 2010/0016761 A1 | 1/2010 | Rosenberg | |
| 2010/0017750 A1 | 1/2010 | Rosenberg et al. | |
| 2010/0022999 A1 | 1/2010 | Gollnick et al. | |
| 2010/0030262 A1 | 2/2010 | McLean et al. | |
| 2010/0049178 A1 | 2/2010 | Deem et al. | |
| 2010/0057056 A1 | 3/2010 | Gurtner et al. | |
| 2010/0081881 A1 | 4/2010 | Murray | |
| 2010/0137799 A1 | 6/2010 | Imai | |
| 2010/0210915 A1 | 8/2010 | Caldwell et al. | |
| 2010/0228182 A1 | 9/2010 | Clark, III et al. | |
| 2010/0228207 A1* | 9/2010 | Ballakur | A61B 17/3203 604/319 |
| 2010/0331875 A1 | 12/2010 | Sonoda et al. | |
| 2011/0028898 A1 | 2/2011 | Clark et al. | |
| 2011/0295230 A1* | 12/2011 | O'Dea | A61M 37/0015 604/506 |
| 2012/0022504 A1 | 1/2012 | Epshtein et al. | |
| 2012/0116375 A1 | 5/2012 | Hennings | |
| 2012/0136280 A1 | 5/2012 | Rosenberg et al. | |
| 2012/0136282 A1 | 5/2012 | Rosenberg et al. | |
| 2012/0165725 A1 | 6/2012 | Chomas et al. | |
| 2012/0197242 A1 | 8/2012 | Rosenberg | |
| 2012/0277587 A1 | 11/2012 | Adanny et al. | |
| 2012/0316547 A1 | 12/2012 | Hennings et al. | |
| 2013/0023855 A1 | 1/2013 | Hennings et al. | |
| 2013/0096596 A1 | 4/2013 | Schafer | |
| 2013/0197315 A1 | 8/2013 | Foley | |
| 2013/0197427 A1* | 8/2013 | Merchant | G06Q 10/02 604/24 |
| 2013/0296744 A1 | 11/2013 | Taskinen et al. | |
| 2014/0025050 A1 | 1/2014 | Anderson | |
| 2014/0031803 A1 | 1/2014 | Epshtein et al. | |
| 2014/0107742 A1 | 4/2014 | Mehta | |
| 2014/0228834 A1 | 8/2014 | Adanny et al. | |
| 2014/0249609 A1 | 9/2014 | Zarsky et al. | |
| 2014/0257272 A1 | 9/2014 | Clark, III et al. | |
| 2014/0276693 A1 | 9/2014 | Altshuler et al. | |
| 2014/0277025 A1 | 9/2014 | Clark, III et al. | |
| 2014/0277047 A1 | 9/2014 | Clark, III et al. | |
| 2014/0277048 A1 | 9/2014 | Clark, III et al. | |
| 2014/0316393 A1 | 10/2014 | Levinson | |
| 2015/0064165 A1 | 3/2015 | Perry et al. | |

FOREIGN PATENT DOCUMENTS

| | | |
|---|---|---|
| CN | 1159908 | 9/1997 |
| CN | 1484520 A | 3/2004 |
| CN | 1823687 | 8/2006 |
| CN | 2007/20159899 | 12/2007 |
| CN | 2011/31982 | 10/2008 |
| CN | 101795641 | 8/2010 |
| DE | 3838530 | 5/1990 |
| DE | 4426421 | 2/1996 |
| EP | 148116 | 7/1985 |
| EP | 0224934 | 12/1986 |
| EP | 0278074 | 1/1987 |
| EP | 0327490 | 2/1989 |
| EP | 0384831 | 2/1990 |
| EP | 0953432 | 3/1999 |
| FR | 2643252 | 2/1989 |
| GB | 1216813 | 12/1970 |
| GB | 1577551 | 2/1976 |
| GB | 2327614 | 3/1999 |
| JP | 57-139358 | 8/1982 |
| JP | 2126848 | 5/1990 |
| JP | 2180275 | 7/1990 |
| JP | 5215591 | 8/1993 |
| JP | 2000-190976 | 7/2000 |
| JP | 2001516625 | 10/2001 |
| JP | 2002-017742 | 1/2002 |
| JP | 2002-528220 | 9/2002 |

(56) References Cited

FOREIGN PATENT DOCUMENTS

| | | |
|---|---|---|
| JP | 2004-283420 | 10/2004 |
| JP | 2005087519 | 4/2005 |
| WO | WO 1980/02365 | 11/1980 |
| WO | WO 1989/05159 | 6/1989 |
| WO | WO1989/05160 | 6/1989 |
| WO | WO1989/09593 | 10/1989 |
| WO | WO1990/01971 | 3/1990 |
| WO | WO1992/09238 | 6/1992 |
| WO | WO1995/15118 | 6/1995 |
| WO | WO 9729701 | 8/1997 |
| WO | WO9913936 | 3/1999 |
| WO | WO9942138 | 8/1999 |
| WO | WO 00/25692 | 5/2000 |
| WO | WO 2000/36982 | 6/2000 |
| WO | WO 03/030984 | 4/2003 |
| WO | WO 03/041597 | 5/2003 |
| WO | WO2003/047689 | 6/2003 |
| WO | WO2004/000116 | 12/2003 |
| WO | WO2004/069153 | 8/2004 |
| WO | WO2005/009865 | 2/2005 |
| WO | WO2005/105282 | 11/2005 |
| WO | WO2005/105818 | 11/2005 |
| WO | WO2006/053588 | 5/2006 |
| WO | WO2007/035177 | 3/2007 |
| WO | WO2007/052662 | 5/2007 |
| WO | WO2007102161 | 9/2007 |
| WO | WO2008/055243 | 5/2008 |
| WO | WO2008/139303 | 11/2008 |
| WO | WO2010/020021 | 2/2010 |
| WO | WO2011/017663 | 2/2011 |
| WO | WO2012/087506 | 6/2012 |
| WO | WO2013/059263 | 4/2013 |
| WO | WO 2014/009875 | 1/2014 |
| WO | WO 2014/009826 | 3/2014 |
| WO | WO 2014/060977 | 4/2014 |
| WO | WO 2014/097288 | 6/2014 |
| WO | WO 2014/108888 | 7/2014 |
| WO | WO 2014/141229 | 9/2014 |

OTHER PUBLICATIONS

Green, Jeremy B. et al. Cellfina observations: pearls and pitfalls, Seminars in Cutaneouse Medicine and Surgery, vol. 34, Sep. 2015, pp. 144-146.

Kaminer, Michael S. et al. Multicenter Pivotal Study of Vacuum-Assisted Precise Tissue Release for the Treatment of Cellulite. American Society for Dermatologic Surgery, Inc. Sermatol Surg 2015:41:336-347 (2015).

Albrecht, T., et al., Guidelines for the Use of Contrast Agents in Ultrasound, Ultraschall in Med 2004, Jan. 2004, nn. 249-256, vol. 25.

Bindal, Dr. V. V., et al., Environmental Health Criteria for Ultrasound, International Programme on Chemical Safety, 1982, on. 1-153, World Health Organization.

Boyer, J. et al., Undermining in Cutaneous Surgery, Dermatol Surg 27:1, Jan. 2001, pp. 75-78, Blackwell Science, Inc.

Brown, Ph.D., S., Director of Plastic Surgery Research, UT Southwestern Medical Center, Dallas, USA, What Happens After Treatment With the UltroShape Device, UltraShape Ltd., Tel Aviv, Israel (2005).

Cartensen, E.L., Allerton Conference for Ultrasonics in Biophysics and Bioengineering: Cavitation, Ultrasound in Med. & Biol., 1987, on. 687-688, vol. 13, Perzamon Journals Ltd.

Chang, Peter P., et al., Thresholds for Inertial Cavitation in Albunex Suspensions Under Pulsed Ultrasound Conditions, IEEE Transactions on Ultrasonics, Ferroelectrics, and Frequency Control, Jan. 200 I, pp. 161-170, vol. 48, No. I.

Chen, Wen-Shiang, Ultrasound Contrast Agent Behavior near the Fragmentation Threshold, 2000 IEEE Ultrasonics Symposium, 2000, pp. 1935-1938.

Dijkmans, P.A., et al., Microbubbles and Ultrasound: From Diagnosis to Therapy, Eur J Echocardiography, 2004, pp. 245-256, vol. 5, Elsevier Ltd., The Netherlands.

Feril, L.B., et al., Enhanced Ultrasound-Induced Apoptosis and Cell Lysis by a Hypnotic Medium, International Journal of Radiation Biology, Feb. 2004, PO. 165-175, vol. 2, Taylor & Francis Ltd., United Kingdom.

Feril, Jr., Loreto B., et al., Biological Effects of Low Intensity Ultrasound: The Mechanism Involved, and its Implications on Therapy and on Biosafety of Ultrasound, J. Radial. Res., 2004, nn. 479-489, vol. 45.

Forsberg, Ph.D., F., et al., On the Usefulness of the Mechanical Index Displayed on Clinical Ultrasound Scanners for Predicting Contrast Microbubble Destruction, J Ultrasound Med, 2005, pp. 443-450, vol. 24, American Institute of Ultrasound in Medicine.

Hanscom, D.R., Infringement Search Report prepared for K. Angela Macfarlane, Esq., Chief Technology Counsel, The Foundry, Nov. 15, 2005.

Hexsel, D. et al, Side-By-Side Comparison of Areas with and without Cellulite Depressions Using Magnetic Resonance Imaging, American Society for Dermatologic Surgery, Inc., 2009, pp. 1-7, Wiley Periodicals, Inc.

Hexsel, M.D., Doris Maria, et al., Subcision: a Treatment for Cellulite, International journal of Dermatology 2000, on. 539-544, vol. 39.

Holland, Christy K., et al., In Vitro Detection of Cavitation Induced by a Diagnostic Ultrasound System, IEEE Transactions on Ultrasonics, Ferroelectrics, and Frequency Control, Jan. 1992, pp. 95-101, vol. 39, No. I.

Farlex "Chamber" <URL: http://www.thefreedictionary.com/chamber>, retrieved Jun. 16, 2013, 4pages.

Internet Web Site—www.icin.nllread/project 21, The Interuniversity Cardiology Institute of the Netherlands, 3 pgs., visited Dec. 22, 2005.

Internet Web Site—www.turnwoodinternational.comiCellulite.htm, Acthyderm Treating Cellulite, Aug. 5, 2005, 4pgs., visited Jan. 12, 2006.

Khan, M. et al., Treatment of cellulite—Part I. Pathophysiology, J Am Acad Dermatol, 2009, vol. 62, No. 3, pp. 361-370.

Khan, M. et al., Treatment of cellulite—Part II. Advances and controversies, JAm Acad Dermatol, 2009, vol. 62, No. 3, pp. 373-384.

Lawrence, M.D., N., et al., The Efficacy of External Ultrasound-Assisted Liposuction: A Randomized Controlled Trial, Dermatol SuII!, Apr. 2000, nn. 329-332, vol. 26, Blackwell Science, Inc.

Letters to the Editor on the Thermal Motions of Small Bubbles, Ultrasound in Med. & Biol., 1984, pp. L377-L379, Pergamon Press Ltd., U.S.A.

Michaelson, Solomon M., et al., Fundamental and Applied Aspects of Nonionizing Radiation, Rochester International Conference on Environmental Toxicity, 75h, 1974, pp. 275-299, Plenum Press, New York and London.

Miller, Douglas 1., A Review of the Ultrasonic Bioeffects of Microsonation, Gas-Body Activiation, and Related Cavitation-Like Phenomena, Ultrasound in Med. & Biol., 1987, pp. 443-470, vol. 13, Pergamon Journals Ltd.

Miller, Douglas 1., et al., Further Investigations of ATP Release From Human Erythrocytes Exposed to Ultrasonically Activated Gas-Filled Pores, Ultrasound in Med. & Biol., 1983, pp. 297-307, vol. 9, No. 3, Pergamon Press Ltd., Great Britain.

Miller, Douglas L., et al., On the Oscillation Mode of Gas-filled Micropores, 1. Acoust. Soc. Am., 1985, pp. 946-953, vol. 77 (3).

Miller, Douglas L., Gas Body Activation, Ultrasonics, Nov. 1984, pp. 261-269, vol. 22, No. 6, Butterworth & Co. Ltd.

Miller, Douglas L., Microstreaming Shear As a Mechanism of Cell Death in Elodea Leaves Exposed to Ultrasound, Ultrasound in Med. & Biol., 1985, op. 285-292, vol. II, No. 2, Pergamon Press, U.S.A.

Miller, Morton W., et al., A Review of In Vitro Bioeffects of Inertial Ultrasonic Cavitation From a Mechanistic Perspective, Ultrasound in Med. & Biol., 1996, nn. 1131-1154, vol. 22, No. 9.

(56) References Cited

OTHER PUBLICATIONS

Nyborg, Dr. Wesley L., Physical Mechanisms for Biological Effects of Ultrasound, HEW Publicaton (FDA) 78/8062, Sep. 1977, pp. 1-59, U.S. Department of Health, Education, and Welfare, Rockville, Maryland.

Orentreich, D. et al., Subcutaneous Incisionless (Subcision) Surgery for the Correction of Depressed Scars and Wrinkles, Dermatol Surg, 1995:21,1995, pp. 543-549, Esevier Science Inc.

Patent Search, CTX System Microbubble Cavitation, Nov. 11, 2005.

Carstensen et al, Biological Effects of Acoustic Cavitation, University of Rochester, Rochester, New York, May 13-16, 1985.

Rohrich,R.J., et al., Comparative Lipoplasty Analysis of in Vivo-Treated Adipose Tissue, Plastic and Reconstructive Surgery, May 2000, 105(6), pp. 2152-2158.

Sasaki, Gordon H. MD, Comparison of Results of Wire Subcision Peformed Alone, With Fills, and/or With Adjacent Surgical Procedures, Aesthetic Surgery Journal, vol. 28, No. 6, Nov./Dec. 2008, p. 619-626.

Scheinfeld, M.D., J.D. Faad, N.S., Liposuction Techniques: External Ultrasound-Assisted, eMedicine.com, Inc., 2005.

Villarraga, M.D., H.R., et al., Destruction of Contrast Microbubbles During Ultrasound Imaging at Conventional Power Output, Journal of the American Society of Echocardiography, Oct. 1997, pp. 783-791.

Vivino, Alfred A., et al., Stable Cavitation at low Ultrasonic Intensities Induces Cell Death and Inhibits H-TdR Incorporation by Con-A-Stimulated Murine Lymphocytes In Vitro, Ultrasound in Med. & Biol., 1985, pp. 751-759, vol. II, No. 5, Pergamon Press Ltd.

Weaver, James C. Electroporation; a general phenomenon for manipulating cells and tissues. J Cell Biochem. Apr. 1993; 51(4):426-35.

* cited by examiner

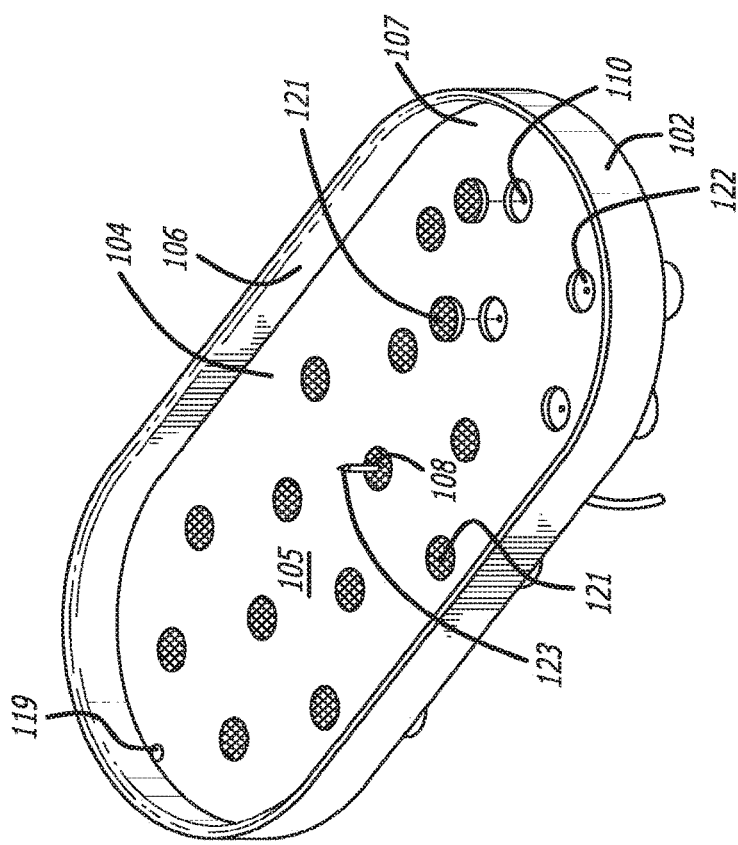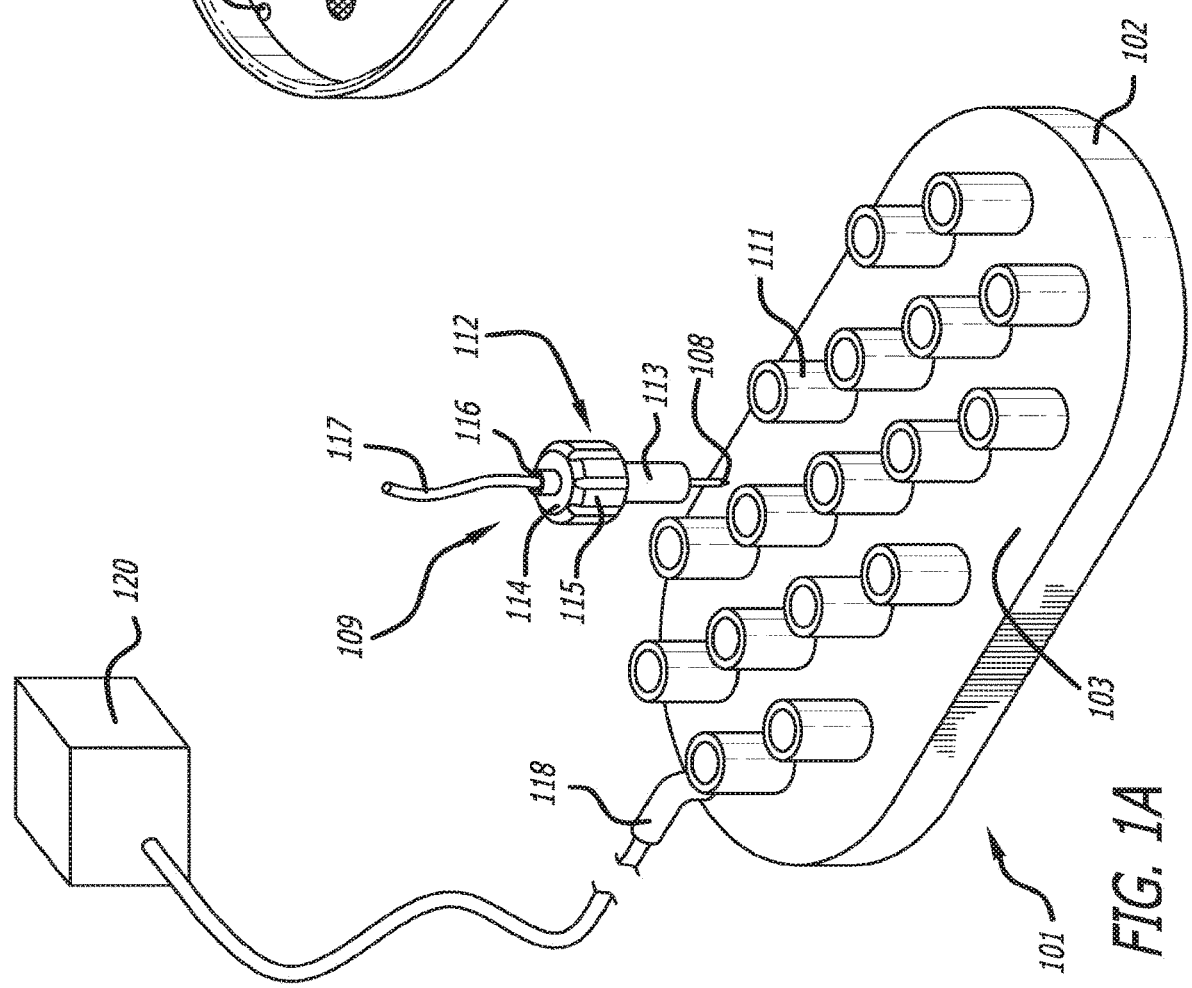

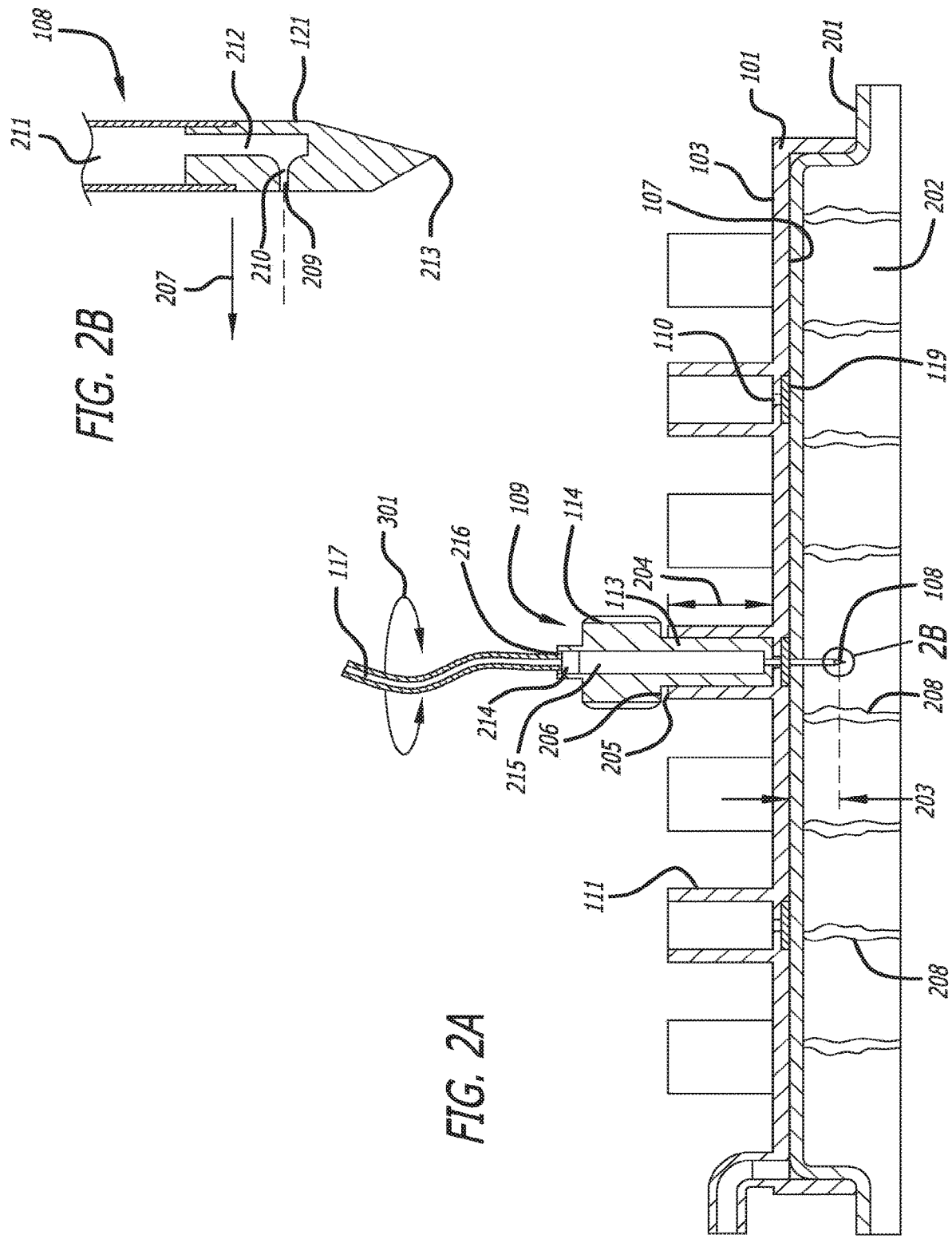

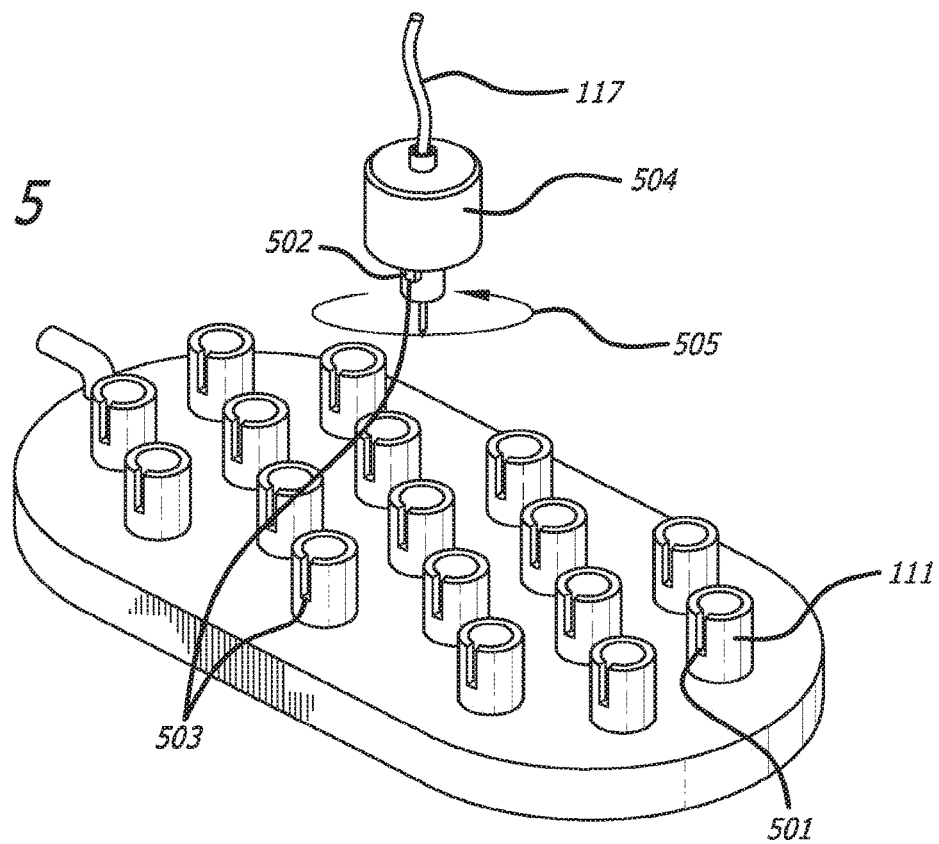
FIG. 5
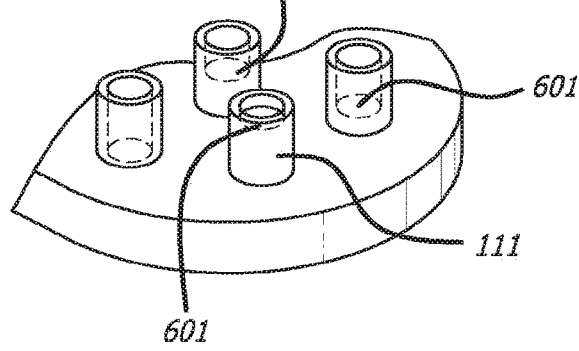
FIG. 6A
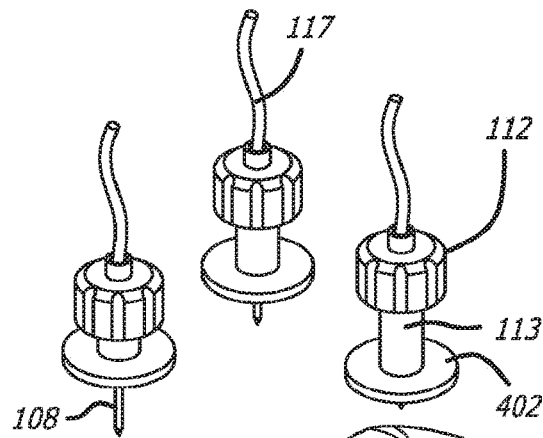
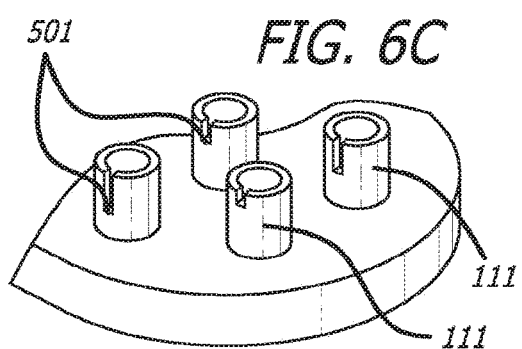
FIG. 6C
FIG. 6B

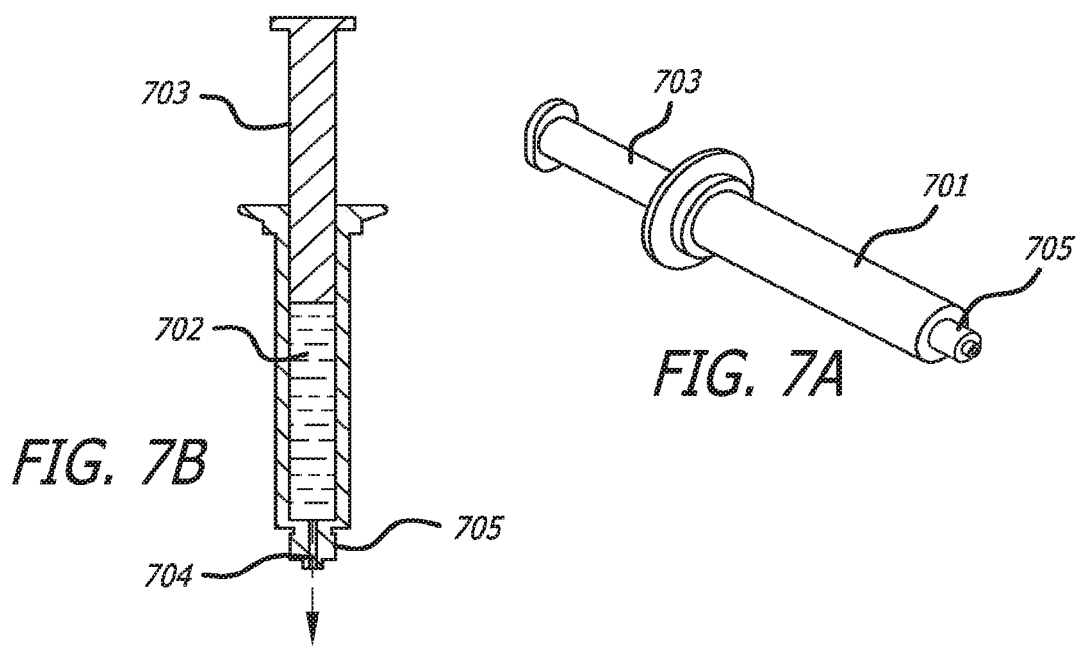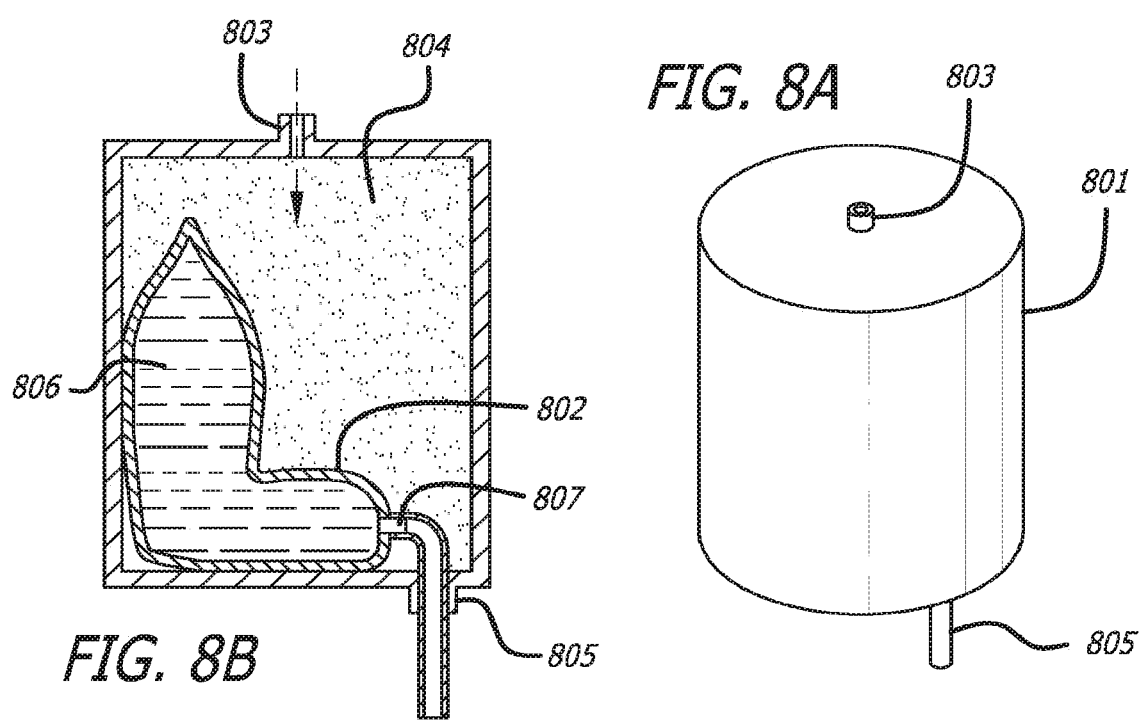

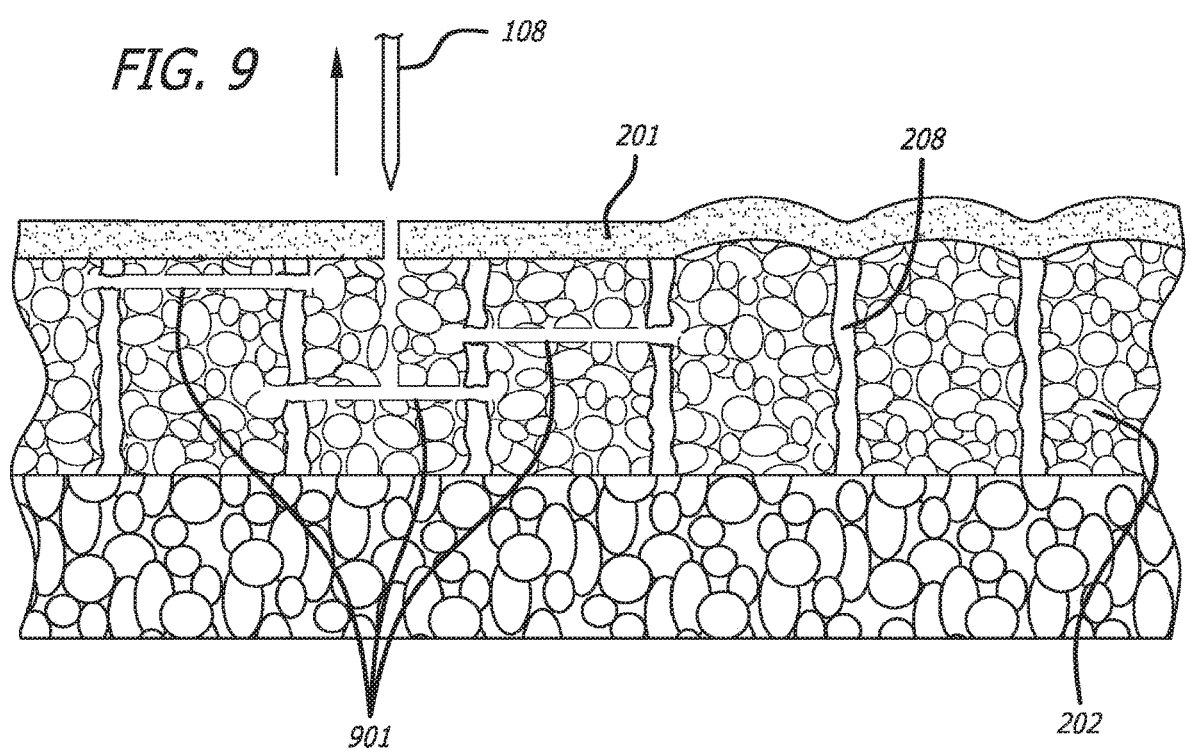

FLUID-JET DISSECTION SYSTEM AND METHOD FOR REDUCING THE APPEARANCE OF CELLULITE

CROSS-REFERENCES TO RELATED APPLICATIONS

This application is a continuation of co-pending U.S. patent application Ser. No. 12/787,377, filed May 25, 2010, the entire contents of which is incorporated by reference herein.

FIELD OF THE INVENTION

The present invention relates to surgical tools and implantable devices which modify subdermal structures for decreasing the appearance of cellulite.

BACKGROUND

Most aesthetic issues for which patients seek treatment from physicians today are "more than skin deep." For instance, gynoid lipodystrophy is a localized disorder of the subcutaneous tissue which leads to an alteration in the topography of the cutaneous surface (skin), or a dimpling effect. It is thought to be caused by increased fluid retention and/or proliferation of adipose tissue in certain subdermal regions, but known to be structure related. This condition, commonly known as cellulite, affects over 90% of post-pubescent women, and some men. Cellulite commonly appears on the hips, buttocks and legs, but is not necessarily caused by being overweight, as is a common perception. Cellulite is formed in the subcutaneous level of tissue, in the subdermal fat layer below the epidermis and dermis layers. In this region, fat cells are arranged in chambers surrounded by bands of connective tissue called septae. Cellulite is in part due to the parallel orientation of these fibrous septae structures. The fibrous structures being oriented in a parallel fashion (and perpendicular to the skin) is unique to women, whereas men typically have more random orientation of fibrous structures. This difference in fibrous structure may be in part or wholly responsible for the fact that men do not exhibit widespread cellulite in comparison to women. As the fat cells held within the perimeters defined by these fibrous septae expand they stretch the septae and surrounding connective tissue. Furthermore, adipocyte expansion from weight gain may also stretch the septae. Eventually this connective tissue contracts and hardens (scleroses) holding the skin at a non-flexible length, while the chambers between the septae continue to expand with weight gain, or water gain. This results in areas of the skin being held down while other sections bulge outward, resulting in the lumpy, 'orange peel' or 'cottage cheese' appearance on the skin surface. Even though obesity is not considered to be a root cause of cellulite, it can certainly worsen the dimpled appearance of a cellulitic region due to the increased number of fat cells in the region.

Over the years, a variety of approaches for treatment of skin irregularities such as cellulite and removal of unwanted adipose tissue have been proposed. For example, methods and devices that provide mechanical massage to the affected area, through either a combination of suction and massage or suction, massage and application of energy, in addition to application of various topical agents are currently available. Developed in the 1950's, mesotherapy is an injection of various treatment solutions through the skin that has been widely used in Europe for conditions ranging from sports injuries to chronic pain, to cosmetic procedures to treat wrinkles and cellulite. This treatment consists of the injection or transfer of various agents through the skin to provide increased circulation and the potential for fat oxidation, such as aminophylline, hyaluronic acid, Novocain, plant extracts and other vitamins. Another treatment entitled Acthyderm (Turnwood International, Ontario, Canada) employs a roller system that electroporates the stratum corneum to open small channels in the dermis, followed by the application of various mesotherapy agents, such as vitamins, antifibrotics, lypolitics, anti-inflammatories and the like.

Various other approaches employing dermatologic creams, lotions, vitamins and herbal supplements have also been proposed to treat cellulite. Private spas and salons offer cellulite massage treatments that include body scrubs, pressure point massage, essential oils, and herbal products using extracts from plant species such as seaweed, horsetail and *clematis* and ivy have also been proposed. Although a multitude of therapies exist, most of them do not provide a lasting effect on the skin irregularity, and some therapies may even cause the worsening of cellulite in certain patients. Yet other treatments for cellulite have negative side effects that limit their adoption. Regardless, most of these therapies require multiple treatments on an ongoing basis to maintain their effect at significant expense and with mixed results.

Massage techniques were tried as early as the 1930's as a method to increase lymphatic drainage and improve the appearance of cellulite. Mechanical massage devices, or Pressotherapy, have also been developed such as the "Endermologie" device (LPG Systems, France), the "Synergie" device (Dynatronics, Salt Lake City, Utah) and the "Silklight" device (Lumenis, Tel Aviv, Israel), all utilizing subdermal massage via vacuum and mechanical rollers. Other approaches have included a variety of energy sources, such as Cynosure's "TriActive" device (Cynosure, Westford, Mass.) utilizing a pulsed semiconductor laser in addition to mechanical massage, and the "Cellulux" device (Palomar Medical, Burlington, Mass.) which emits infrared light through a cooled chiller to target subcutaneous adipose tissue. The "VelaSmooth" system (Syneron, Inc., Yokneam Illit, Israel) employs bipolar radiofrequency energy in conjunction with suction massage to increase metabolism in adipose tissue, and the "Thermacool" device (Thermage, Inc., Hayward, Calif.) utilizes radiofrequency energy to shrink the subdermal fibrous septae to treat wrinkles and other skin defects. Other energy-based therapies such as electrolipophoresis, using several pairs of needles to apply a low frequency interstitial electromagnetic field to aid circulatory drainage have also been developed. Similarly, non-invasive ultrasound is used in the "Dermosonic" device (Symedex Medical, Minneapolis, Minn.) to promote increased fat reabsorption and drainage of retained fluids and toxins.

Methods and devices using ultrasound to disrupt subcutaneous tissues directly has been described in the known art. Such techniques may utilize a high intensity ultrasound wave that is focused on a tissue within the body, thereby causing a localized destruction or injury to cells. The focusing of the high intensity ultrasound may be achieved utilizing, for example, a concave transducer or am acoustic lens. Use of high intensity focused ultrasound to disrupt fat, sometimes in combination with removal of the fat by liposuction, has been described in the known prior art. Such use of high intensity focused ultrasound is distinguished from low acoustic pressure, therapeutic ultrasound.

Recently, it is has also become possible to exploit ultrasound waves for the purpose of disrupting tissue and tissue ablation without heating tissue to a level of tissue disruption. One such device is disclosed in U.S. Publication No. 2007/0055179 to Deem et al., incorporated herein by reference, which includes a method of infiltrating exogenous microbubbles into the target tissue, followed by applying low acoustic pressure ultrasound to the infiltrated tissue to cavitate the bubbles and destroy the target tissue without direct thermal injury to the dermis. Although low acoustic pressure ultrasound may somewhat heat tissue, the tissue is not heated sufficiently to cause direct tissue disruption or to enhance the ablation, and thus significantly reduces the risk of thermal damage to the dermis and associated structures (nerves, hair follicles, blood vessels). Liposonix (Bothell, Wash.) and Ultrashape (Tel Aviv, Israel) employ the use of focused ultrasound to destroy adipose tissue noninvasively. In addition, cryogenic cooling has been proposed for destroying adipose tissue.

Certain other techniques known as liposuction, tumescent liposuction, lypolysis and the like, target adipose tissue in the subdermal and deep fat regions of the body. These techniques may include also removing the fat cells once they are disrupted, or leaving them to be resorbed by the body's immune/lymphatic system. Liposuction is the most commonly performed cosmetic surgical procedure. Traditional liposuction includes the use of a surgical cannula placed at the site of the fat to be removed, and then the use of an infusion of fluids and mechanical motion of the cannula to break up the fatty tissue, and suction to "vacuum" the disrupted fatty tissue directly out of the patient. A variation on the traditional liposuction technique known as tumescent liposuction was introduced in 1985 and is currently considered by some to be the standard of care in the United States. It involves the infusion of tumescent fluids to the targeted region prior to mechanical disruption and removal by the suction cannula. The fluids may help to ease the pain of the mechanical disruption in some patients, while also swelling the tissues to make them more susceptible to mechanical removal. Various combinations of fluids may be employed in the tumescent solution including a local anesthetic such as lidocaine, a vasoconstrictive agent such as epinephrine, saline, potassium and the like. The benefits of such an approach are detailed in the articles, "Laboratory and Histopathologic Comparative Study of Internal Ultrasound-Assisted Lipoplasty and Tumescent Lipoplasty" Plastic and Reconstructive Surgery, September 15, (2002) 110:4, 11581164, and "When One Liter Does Not Equal 1000 Milliliters: Implications for the Tumescent Technique" Dermatol. Surg. (2000) 26:1024-1028, the contents of which are expressly incorporated herein by reference in their entirety.

Traditional fat extraction techniques such as liposuction, target deep fat and larger regions of the anatomy and can sometimes worsen the appearance of cellulite. The subdermal fat pockets remain and are accentuated by the loss of underlying bulk (deep fat) in the region. Many times liposuction is performed and patients still seek therapy for remaining skin irregularities, such as cellulite. The tools used in these procedures often have cutting edges and are intended to dissect the subcutaneous tissue and fibrous septae. Representative of such conventional tools is the "Toledo" cannula, pictured in Toledo L S, Mauas R, Complications of Body Sculpture: Prevention and Treatment. Clin Plastic Surg. 2006:33; 1-11.

There are physicians who target the more shallow subdermal fat pockets with liposuction, but at a higher risk of directly creating surface irregularities rather than treating them. Liposuction is not considered a viable treatment for cellulite for these reasons.

Another issue that must be factored in with liposuction is the amount of drugs infused with the tumescent solution. With large volume liposuctions, the Lidocaine infusion (for pain) can get up as high as 50 mg/kg, well above the intravascular toxicity limit of 7 mg/kg. The reason why liposuction patients can tolerate such a large volume of lidocaine is that the lidocaine is injected subcutaneously, is highly diluted, and is absorbed slowly over time. Thus, the actual systemic level of lidocaine is lower. However, in some cases lidocaine can spill over into the circulation and has resulted in patient mortality. For this reason, physicians monitor the Lidocaine does closely and often limit the area or treatment as a result.

More recently, energy sources have been added to the cannula to assist in the break-up and liquefication of the fat which in turn improves the ease of use. The "Lysonix" system (Mentor Corporation, Santa Barbara, Calif.) and "Vaser" system (Sound Surgical, Louisville, Colo.) utilize an ultrasonic transducer within the suction cannula to assist in tissue disruption (by cavitation of the tissue at the targeted site). Laser assisted cannula are offered by several companies including "Smartlipo" (Cynosure, Westford, Mass.), "Slimlipo" (Palomar Medical, Burlington, Mass.), and "Smoothlipo" (Eleme Medical, Merrimack, N.H.).

Subcutaneous dissection without fat aspiration is another approach to the treatment of skin irregularities such as scarring and dimpling. A technique called "subcision" was described by Orentreich in 1995. See Orentreich D S, Orentreich N. Subcutaneous incisionless surgery for the correction of depressed scars and wrinkles. Dermatological Surgery 1995 June; 21 (6): 543-9 This technique involves the insertion of a relatively large gauge needle subdermally in the region of dimpling or scarring, and then mechanically manipulating the needle below the skin to break up the fibrous septae in the subdermal region. In at least one known method of subcision, a solution containing an anesthetic (Lidocaine) and vasoconstrictor is injected into the targeted region and allowed to take effect. An 18-gauge needle is then inserted 10-20 mm below the cutaneous surface. The needle is then pulled back and directed parallel to the epidermis to create a dissection plane beneath the skin to essentially tear through, or "free up" the tightened septae causing the dimpling or scarring. Pressure is then applied to control bleeding acutely, and then by the use of compressive clothing following the procedure. While clinically effective in some patients, pain, bruising, bleeding and scarring can result. Other cutting implements include the aforementioned Toledo cannula, and several string or wire based cutting methods including the "Surgiwire" (Coapt Systems, Palo Alto, Calif.) and "ReleaseWire" (MicroAire, Charlottesville, Va.).

Cutting or relieving of the fibrous septae in the subdermal region by current subcision methods, is labor intensive, time consuming and techniques are highly variable. Significant physician time must be devoted to the procedure and there are technical limits as well as anesthetic limits to the size of a treatable area. There is a lack of clinical proof of that the techniques work for most patients and that the effects are lasting. For these reasons, and because of the potential side effects and extended time required for healing, subcision and liposuction have largely been abandoned as a treatment for cellulite in the United States.

In light of the foregoing, it would be desirable to provide a device and method for treating skin irregularities such as cellulite and to provide a sustained aesthetic result to a body region, such as the face, neck, arms, legs, thighs, buttocks, breasts, stomach and other targeted regions. It would also be desirable to provide device and method for treating skin irregularities that enhance prior techniques and make them less time intensive, more controlled, minimally invasive, and subject the patient to fewer side effects. The present invention adds a minimally invasive device and method for skin treatment by providing a controlled and less traumatic means for subcutaneous dissection and cutting of the fibrous septae in the subdermal fat or in the layer between the subdermal fat layers and the dermis, responsible for the appearance of cellulite. The device and method also provides an even level of cutting, parallel to the surface of the skin and with adequate skin traction, without further puncture or cutting of the skin. In addition to treating cellulite, this device and method may be used to treat hyperhidrosis, acne or other scars, and wrinkles. This treatment may also be used in conjunction with known methods of removing fat, skin tightening, or dermal thickening.

SUMMARY OF THE INVENTION

A system for minimally invasive skin treatment is disclosed. In some aspects, the system includes a platform having a perimeter elevation and a top which cooperatively define a recessed area with an inner side of the perimeter elevation and top defining an apposition surface facing into the recessed area. An injection port is provided and positioned about an entry hole through the top of the platform. The system further includes an injection device having a needle. The injection device is configured to be slidably disposed in the injection port such that a distal end of the needle passes through the entry hole into the recessed area and is also removably secured perpendicular to the platform, and configured to discharge a fluid in a direction orthogonal to an axis of the needle and parallel to the top of the platform. In some aspects, the distal end of the needle has a nozzle flush with a side of the needle. In some aspects the injection port is a cylinder; however, the port can be square, ovoid, rectangular, triangular, a polygon, or other shape without deviation from the scope of the invention.

In some aspects, the injection device may have a base and an upper body, and wherein an outer perimeter of the base snuggly fits within an inner perimeter of the selected injection port. In some aspects, the outer perimeter of the base of the injection device is smaller than an outer perimeter of the upper body of the injection device. In these aspects, the injection port is preferably raised above the top of the platform such that a bottom rim of the upper body rests flush upon a top rim of the injection port when the injection device is fully inserted into the injection port. The top rim of the injection port, in some aspects, may have a notch and the injection device has a keyed protrusion located proximal an interface between the base and the upper body of the injection device. To that end, the keyed protrusion fits within the notch when the bottom rim of the upper body is flush upon the top rim of the injection port, such that the injection device is prevented from rotating relative to the platform. In other aspects, the injection port is a recessed bore in the top of the platform about the entry hole, and the injection device includes a disk having a shallow boss on a bottom of the disk, wherein the shallow boss is configured to snuggly fit within the recessed bore such that a bottom of an outer perimeter of the disk rests upon the top surface about the injection port when the injection device is disposed in to the injection port.

In some aspects, the system may also include a mechanism for automatically rotating the needle. In some aspects, multiple injection ports are provided on the platform, and each of the injection ports are positioned about a corresponding entry hole through the top of the platform.

Further aspects of the system may include a vacuum fitting operably connected to one of the top of the platform and the perimeter elevation of the platform and in fluid communication with the recessed area, and a vacuum pump in fluid communication with the vacuum fitting, wherein the vacuum pump is configured to supply a suction force to the recessed area to pull a tissue snugly and securely against the apposition surface when the recessed area is placed over the tissue. In these aspects, each of the multiple injection ports may be sealed to maintain an applied vacuum. In some aspects, this is accomplished by covering each of the ports with an elastomeric septum, the elastomeric septum being configured to be pierced by the needle and to substantially self-seal when the needle is removed such as to substantially prevent a vacuum leakage from the recessed area when the suction force is supplied.

The system may also include a rigid pressure canister including a source of a solution and a supply exit port, wherein the canister is filled with a pressurized gas and the source of the solution is in fluid communication with the injection device and the needle. The source of the solution may be a flexible bag inside the rigid pressure canister, the flexible bag being at least partially filled with a solution, and wherein the solution is in fluid isolation from the pressurized gas. The system may yet further include a high-pressure syringe having a syringe pump, wherein the syringe is in fluid connection with the needle, and wherein the syringe is configured to inject a solution through the needle when the syringe pump is actuated.

In certain aspects of the system the nozzle is configured to increase a kinetic energy of a solution injected by the injection device through the needle. In some aspects, the syringe may include a passage at its distal end, the passage being configured to increase a kinetic energy of the solution when it is injected by the injection device. In some aspects, the nozzle may be a convergent nozzle, and wherein a throat of the nozzle converges toward the side of the needle. In some aspects, the interior of the needle may narrow near the distal end of the needle and downstream of the throat of the nozzle. In one aspect, the needle may have a hollow channel interfacing with the nozzle but terminating above a hardened and sharpened tip for piercing the skin.

In some aspects, the injection device may include a handpiece, and wherein the injection device is configured to be rotated relative to the platform and moved vertically along an axis of the injection port to control a depth of the nozzle relative to the apposition surface. The injection device may also include a swivel fitting for rotatably and fluidically coupling a tubing to the injection device such that the injection device can be rotated relative to the tubing.

A method for minimally invasive skin treatment is also disclosed. The method preferably includes the steps of (1) positioning a platform having a recessed area over a dermis, the platform having an injection port and an entry hole through a top of the platform; (2) applying a force to the platform to move a portion of the dermis into the recessed area to substantially fill the recessed area, such that the portion of the dermis is in contact with an inner surface of the platform and a subcutaneous tissue is disposed in the recessed area; (3) providing an injection device having a needle; (4) inserting a distal end of the needle through the injection port and through the entry hole such that a portion of the injection device is slidably disposed in the injection port and the injection device is secured perpendicular to the platform and the distal end of the needle is percutaneously inserted through the dermis and into the subcutaneous tissue; and (5) discharging at a pressure between 20 and 150 Bar a fluid through a nozzle in a side of the distal end of the needle and inside the subcutaneous tissue, the discharge being substantially parallel to the top of the platform.

In some aspects, the method may further include (5) removing the distal end of the needle from the injection port and the first subcutaneous tissue, (6) inserting a distal end of the needle through a second proximal injection port such that the injection device is secured perpendicular to the platform and the distal end of the needle is percutaneously inserted through the dermis and into the second subcutaneous tissue, and (7) discharging at a pressure between 20 and 150 Bar a fluid through a nozzle in a side of the distal end of the needle and inside the second subcutaneous tissue, the discharge being substantially parallel to the top of the platform. In some aspects, discharging the fluid includes rotating the nozzle to cut fibrous septae in a substantially circular direction in the first and second subcutaneous tissue. In further aspects, the first and second subcutaneous tissue are cut at different depths below the dermis.

In further aspects the method may include piercing an elastomeric septum covering the entry hole with the distal end of the needle. In some aspects the distal end of the needle is positioned such that the nozzle is maintained in the subcutaneous tissue at a selected depth, the depth selected from between 1 mm and 15 mm below the portion of the dermis in contact with the inner surface of the platform. In such aspects, the method may also include rotating the injection device to rotate the distal end of the needle while maintaining the depth of the nozzle in the subcutaneous tissue and an orthogonal positioning of the injection device relative to the platform. In a yet further aspect, the pressure is set above 50 Bar.

A further system for minimally invasive skin treatment is also disclosed. In this aspect, the system includes a recessed platform having a perimeter elevation and a top which cooperatively define a recessed area. An inner side of the perimeter elevation and the top define an apposition surface facing into the recessed area. Also included is a vacuum fitting operably connected to one of the top of the platform and the perimeter elevation of the platform and in fluid communication with the recessed area, and a vacuum pump in fluid communication with the vacuum fitting. The vacuum pump is preferably configured to supply a suction force to the recessed area to pull a tissue snugly and securely against the apposition surface when the recessed area is placed over the tissue. Multiple injection ports are provided on the platform and raised above the top of the platform, each injection port positioned about an entry hole through the top of the platform. Additionally, the system includes an injection device having a needle and a needle housing, the housing including an upper body and a base, the upper body including a handpiece and having a larger diameter than the base, the base being configured to be slidably disposed in a selected injection port such that a portion of the needle passes through a corresponding entry hole and the injection device is removably secured perpendicular to the platform in a manner such that a bottom rim of the upper body rests flush upon a top rim of the selected injection port when the injection device is fully inserted into the injection port. A distal end of the needle preferably has a nozzle flush with a side of the needle and is configured to discharge a fluid at a pressure between 20 and 150 Bar in a direction orthogonal to an axis of the needle and parallel to the top of the platform, and each of the multiple injection ports are preferably covered by an elastomeric septum, wherein the elastomeric septum is configured to be pierced by the needle and to substantially self-seal when the needle is removed such as to substantially prevent a vacuum leakage from the recessed area when the suction force is supplied.

BRIEF DESCRIPTION OF THE DRAWINGS

FIGS. 1A and 1B depict a top and bottom perspective view of a dissection platform having multiple ports for placement of an injection device configured to cut subcutaneous tissue;

FIGS. 2A and 2B depict a cut-away side view of the platform and injection device in use on a dermis of a patient, including an exploded view of an injection nozzle;

FIG. 5 depicts an embodiment of the injection device including a rotary mechanism;

FIGS. 6A through 6C depict further embodiments of the injection ports;

FIGS. 7A and 7B depict a high pressure syringe for use with the injection device; and FIGS. 8A and 8B depict a rigid pressure canister including a pressurized gas and a solution for use with the injection device.

FIG. 9 depicts a side view of a plurality of treatment sites made at different treatment depths.

DETAILED DESCRIPTION OF THE PREFERRED EMBODIMENTS

Figure 3:
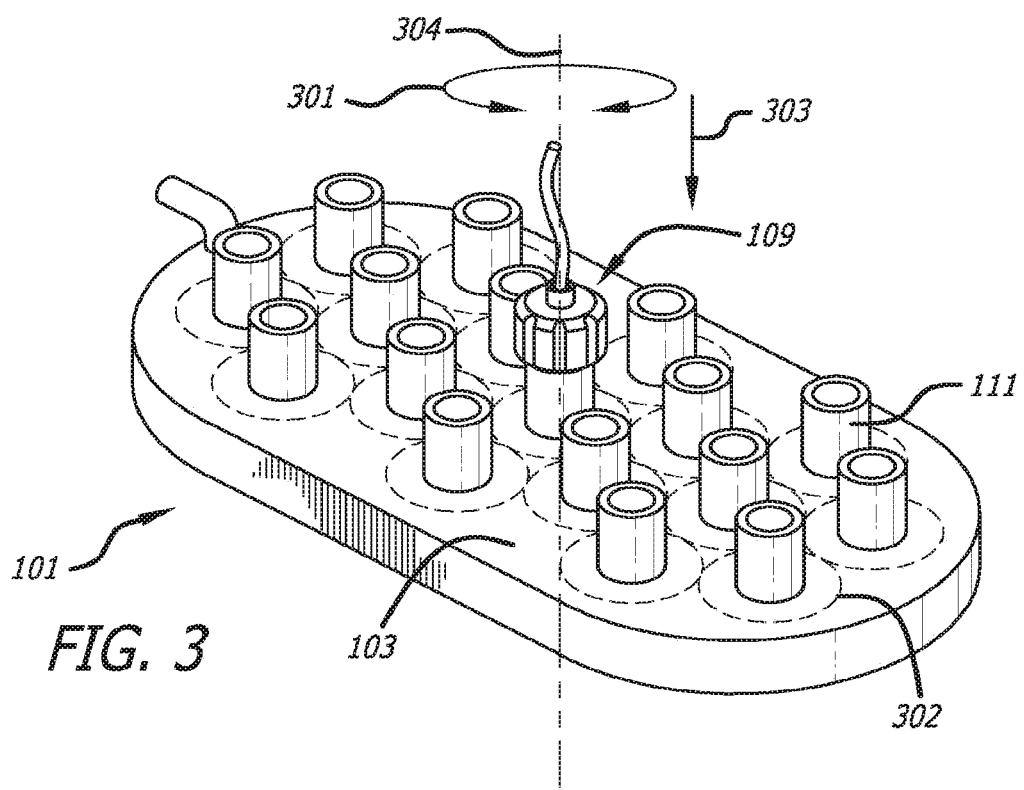
FIG. 3 depicts a perspective view of the platform, including the direction of insertion and rotation and diameter of the cutting action.

As depicted by FIGS. 1A and 1B, an embodiment of the system utilizes a platform 101 to capture and control a location of the skin, or dermis. Platform 101 preferably includes a downwardly extending wall or perimeter elevation 102 about the perimeter of platform 101 such that a bottom side of top 103 of platform 101 and perimeter elevation 102 collectively form recessed area 104 which can be placed over the dermis of a patient. An inner surface 105 of top 103 and inner side 106 perimeter elevation 102 further collectively form an apposition surface 107. By applying a force to the top of platform 101 or by a vacuum supplied to recessed area 104, a portion of a dermis can be moved in to recessed area 104 and against apposition surface 107 to substantially fill the recessed area, thus capturing it and providing some control over the area of tissue captured. This allows a needle 108 disposed on an injection device 109 to be inserted through an entry or through-hole 110 in top 103 of platform 101 and percutaneously though the tissue disposed in the recessed area, and into the subcutaneous tissues encompassed by the recessed area. A high pressure fluid jet is ejected from a side of the needle in such a way as to cut a surgical lesion of a predetermined shape inside the subcutaneous tissues within the recessed area and parallel to the top 103 of platform 101. For the purposes of this disclosure fluid is defined as any biocompatible fluid, for example, saline or water. In some embodiments, the fluid may also include a local anesthetic or pain relieving solution, a vasoconstrictor, an antibiotic, a steroid in normal or buffered saline, or a combination of treatment solutions useful in similar medical procedures. The surgical lesion (dissection) is targeted to be in a range from as shallow as between 1 mm and 2 mm above the interface between the dermis and the shallow fat, to as deep as 20 mm below the skin/fat interface. Applicants hereby define percutaneous to mean a puncture or incision through the skin, typically, between 0.4 mm and 4.0 mm.

Platform 101 may include one or more through-holes 110. As depicted by FIG. 1A, one or more injection ports 111 may be coupled to the top 103 of platform 101 about a respective through-hole 110. The purpose of the injection port is to provide stability and support for injection device 109 when needle 108 is inserted through hole 110.

Injection device 109 includes needle 108 and a needle housing 112. In the depicted embodiment, needle housing 112 includes a base 113 and an upper body 114. Upper body 114 may further include grips 115 that make up a handpiece for manual control or positioning of device 109. The outer perimeter of base 113 is sized slightly smaller than the inner perimeter of a selected injection port 111 so that injection device may be slidably inserted into injection port 111. In the depicted embodiment, injection port 111 is a cylinder fixed to top 103 of platform 101, however, as shown by other embodiments herein, injection port 111 can be any number of configurations that meet the purpose of providing support to injection device 109 and needle 108. In the depicted embodiment, injection port 111 is substantially circular in shape, however, injection port 111 can also be any shape, such as a square, rectangle, triangle, polygon, ovoid. Moreover, the depicted embodiment is configured for multiple ports 111, however, some embodiments may only include a single port. In some embodiments, injection device 111 may further include a connector 116 for connecting to a solution-supply tubing 117 to provide a fluidic connection to needle 108 for injection of a solution.

In some embodiments, a vacuum (suction) is used to enhance the capture of tissue within recessed area 104 and against apposition surface 107. A vacuum port 118 is provided on platform 101 and in fluid connection with one or more suction holes 119 disposed within inner surface 105. A vacuum pump 120 may be connected to port 118 to provide a suction to recessed area 104. In those embodiments including a vacuum to move a dermis into recessed area 104 and against apposition surface 107 a membrane formed of a flexible and resilient material may also be applied to apposition surface 107, and across through-holes 110 to minimize vacuum leakage there through. In the depicted embodiment, each through-hole 110 has its own individual membrane 121. Disposed about each through-hole 110 is an inner indentation 122 in inner surface 105 of platform 101. Each indentation 122 is larger than through-hole 110 and provides a recessed space for insertion of an individual membrane 121. The intent is that each membrane would be flush with the skin-side surface of the vacuum platform 101. When injection device 109 is inserted into injection port 111 and needle 108 passes through hole 110, a distal end 123 of needle 108 pierces through membrane 121 and is inserted into recessed area 104. The membrane is preferably snugly secured in indentation 122 and sufficiently resilient to seal around (self-sealing) needle 108 as it pierces therethrough. The membrane may be formed of silicone or other similar material. FIG. 1B depicts some indentations 122 filled with a membrane 121 and others that are empty. In some embodiments all indentations 122 will be filled, while, in other embodiments, none, one or less than all indentations will be filled. In one embodiment, a single membrane/septum covers the entire inner surface of the vacuum platform to cover all through-holes 110. In such an embodiment, indentations 122 may be omitted and inner surface 105 remains flush about through-holes 110.

FIG. 2A depicts platform 101 in use with a vacuum pressure (suction) applied to a portion of a skin tissue 201. Suction applied at vacuum port 116 causes skin 201 to be pulled up into contact with apposition surface 107 of platform 101. By applying a sufficient suction force, a portion of epidermis 201 is pulled into recessed area 104 of platform 101 and conforms to inner recessed area 104. While the surface of the skin 201 is tightly positioned against apposition surface 107, including perimeter elevation 102 of recessed area 104, fat layer 202 (subcutaneous tissue) is also drawn into recessed area 104. Needle 108 or other cutting tool (e.g., blade, wire, RF probe, laser) can be inserted through injection port 111 and through entry hole 110, through skin 201, and into subcutaneous tissue 202. Significantly, the platform enables the needle or other cutting tool to be consistently inserted into a desired treatment depth 203 (measured orthogonally from the dermis). In the depicted embodiment in which injection port 111 is a raised above the top 103 of platform 101, and has a height 204 greater than base 113 of injection device 109, the top rim 205 of injection port 111 provides a stop against further insertion of injection device 109 within port 111. When fully inserted the bottom rim 206 of upper body 113 comes to rest against top rim 205 preventing further insertion of injection device 109. Platform 101 thus provides for precise control of the depth of needle 108 within tissue 202 and of the dissection plane and allows for cutting substantially parallel to the surface of the tissue along a plane parallel to the surface of the skin.

In some embodiments needle 108 is configured to increase a kinetic energy of the solution when it is injected by the injection device. Injection device 109 is used to inject a solution in a direction 207 away from needle 108 and at a high pressure parallel to the surface of the dermis, and at depth 203, to cut fibrous septae 208 located in a treatment area located in the subcutaneous tissue 202. It has been determined that a pressure of between 20 and 60 Bar will sustain a fluid-jet with sufficient cutting power to cut 8 mm into subcutaneous tissue in one single pass or rotation of the needle. Deeper cuts can be achieved by repeated application on the same cut. Fluid-jet dissection can also lead to a fluid uptake of the cut tissue. Morphologically all the vessels, lying in the cut are undamaged if the pressure doesn't exceed 40 Bar pressure range. It has been found, in some embodiments, that setting the pressure to above 50 Bar ensures that the fibrous septae 208 located in the treatment area is cut. In some embodiments, for example, the pressure is set above 50 Bar. In some embodiments, the pressure is set between 50 and 60 Bar.

Needle 108 includes a nozzle 209 on a side of the distal end 213 of the needle. Preferably, nozzle 208 is configured to increase a kinetic energy of a solution injected by the injection device through the needle. In some embodiments, such as that depicted by FIG. 2B, nozzle is a convergent nozzle. Thus, the throat 210 of the nozzle converges toward the side of the needle. In some embodiments, the interior 211 of the needle narrows near the distal end of the needle, but upstream of throat 210 of the nozzle. In some embodiments, this narrowing includes a hollow channel 212 that interfaces with nozzle 209 but terminates above a hardened and sharpened tip 213 configured for piercing the skin 201. In other embodiments, the nozzle may be a divergent nozzle and/or be configured to slow the kinetic energy of the solution injected. It may be desirous to use injection device 109 at a lower pressure but high enough to saturate the treatment area with a solution, for example, a medicament, such as lidocaine and/or epinephrine, prior to or after performing a cutting action or creating a lesion within the treatment area.

FIG. 2A further details how needle 108 may be configured in fluid connection with tubing 115. In those embodiments utilizing an external solution source (e.g., FIGS. 7 and 8) tube 115 may be connected to a swivel fitting 214 near a top of housing 112. Swivel fitting 214 preferably divides a lower needle lumen portion 215 and solution supply tubing 117, each configured to rotate independently from each other. The fitting is includes an upper and lower sections (not shown). The lower fitting section is connectable lumen portion 215. The upper section extends through an orifice 216 in upper body 114. In this manner the lower section of fitting 214 may remain fixed with a rotating injection device 109 while upper section may remain fixed with tubing 117, such that the injection device 109 may spin relative to tubing 117. In this manner, tubing 117 is kept in fluid connection with needle 108 and in fluid isolation with housing 112 of injection device 109 and the rest of the system.

Laser can also be used to cut fibrous septae. Laser cutting is dependent on the wavelength chosen, because the optothermal process becomes safe and efficient when a wavelength is chosen that is close to the absorption coefficient of the tissue to be cut (tissues, selectively absorb light of a particular color). Commonly used Laser wavelengths—for surgery etc—are 10.6 micro m (Carbon dioxide laser); 2.1 micro m (laser diode), 700-840 nm (laser diode). As found by Misbah H. Khan et al., *Treatment of Cellulite*, J. AM. ACAD. DERMATOL. (March 2010), at 379, incorporated herein by reference, one preferred wavelength for fat-melting (laser liposuction) is 940 nm. Other laser-lipo devices use wavelengths that are greatly absorbed by water. These include wavelengths in the short (1.4-3 micro m) to mid-wavelength (3-8 micro m) infra red range.

In one embodiment, the cutting is performed by laser rather than fluid-jet. In this embodiment, the laser is a multi-wavelength device—one wavelength could one that is most absorbed by water and commonly used (980 nm, 810, 10.6 micro-m). In further embodiments, the wavelength can be customized for fat melting (940 nm) or connective tissue structural destruction (for collagen, i.e., between 6 and 7 micro m). The kind of waveguide (articulation arm, fibre or hollow) will generally depend on the type of laser source. For use in this embodiment, however, a 'fibre' waveguide is used (i.e., replacing nozzle 209), and is generalized enough to be compatible with many wavelengths of laser. Focused laser can be achieved both by waveguide design and by using a lens at the end of the fibre. Focused laser can be used for cutting, while defocused laser can be used for coagulation only purposes. Depth of penetration is dependent on the wavelength selected and the minimum beam spot size. The beam spot size depends on the diameter of the fibre and the wavelength. In general, decreasing the wavelength, decreases the spot size & smaller the spot size, the smaller the depth of penetration. The power/intensity of the laser used is about between 20 and 40 W to cut fibrous septae.

FIG. 3 depicts an embodiment of the system in use. The needle housing 112 is rotated 301 about its axis 304. The angle of rotation is preferably 360 degrees but can be 90 degrees, 180 degrees or any suitable angle for targeting the subcutaneous area to be treated. In the depicted embodiment, housing 112 is rotated 360 causing the fluid jet to make a circular-planar cut 302 in tissue 202. Needle housing 112 can be rotated manually by the user, or by electrical or mechanical means (e.g., FIG. 5).

Platform 101 is first placed over dermis 201. A portion of the dermis is then moved into recessed area 104 by a vacuum or manual pressure on top 103 of platform 101 (FIG. 2A). This causes the portion of the dermis in contact with inner surface 105 of the platform and subcutaneous tissue 202 to be disposed in recessed area 104. Injection device 109 is then inserted 303 along axis 304, or slidably disposed, in injection port 111 and distal end 123 of needle 108 moved through entry hole 110 (FIG. 1B). When appropriately configured, a portion of the needle housing is slidably disposed in the injection port and the injection device is secured perpendicular to the platform and the distal end of the needle is percutaneously inserted through the dermis and into the subcutaneous tissue. A solution is then discharged into subcutaneous tissue 202 at a pressure between 20 and 150 Bar through nozzle 209 in a side of the distal end of the needle, the discharge being substantially parallel to the top of the platform. In one embodiment, the pressure is set between 20 and 60 Bar. In further embodiments an elastomeric septum 121 covering the entry hole is pierced with the distal end of the needle. In some embodiments the distal end of the needle is positioned such that the nozzle is maintained in the subcutaneous tissue at a selected depth 203. In some embodiments, depth 203 is selected from between 1 mm and 15 mm below the portion of the dermis in contact with apposition surface 107 of platform 101. The device typically controls a depth 203 of between 1 mm and 15 mm below the surface of skin (measured orthogonally from the dermis); but a depth less than 1 mm or greater than 15 mm is also contemplated. Depth 203 is generally defined as being measured from apposition surface 107. For the purpose of this disclosure, however, the measurement is taken when epidermis 201 is flush against apposition surface 107 and the thickness of epidermis is considered negligible. As such, depth 203 can also be considered to be a depth below the surface of the skin or a depth below epidermis 201. The method may also include rotating the housing to rotate the distal end of the needle while maintaining the depth of the nozzle in the subcutaneous tissue and an orthogonal positioning of the injection device relative to the platform.

When needle housing 112 is rotated 301, the diameter of circular cut 302 is controlled by various parameters, including the geometry of the exit nozzle 209, the speed of rotation, and the pressure of the fluid supply. In one embodiment, the pressure is set relatively low at 20 to 40 Bar to infuse a solution into the treatment area. In further embodiments, the pressure is set relatively high so as to (e.g., between 40 and 60 Bar) to displace and/or sever fibrous septae. In some embodiments, the spacing between platform through-holes 110 is chosen in conjunction with the cutting diameter of the fluid jet, so as to achieve the desired coverage efficiency. The system may also be configured such that treatment depths at adjacent sites are not identical, so as to prevent interconnecting the cut regions.

Figure 4:
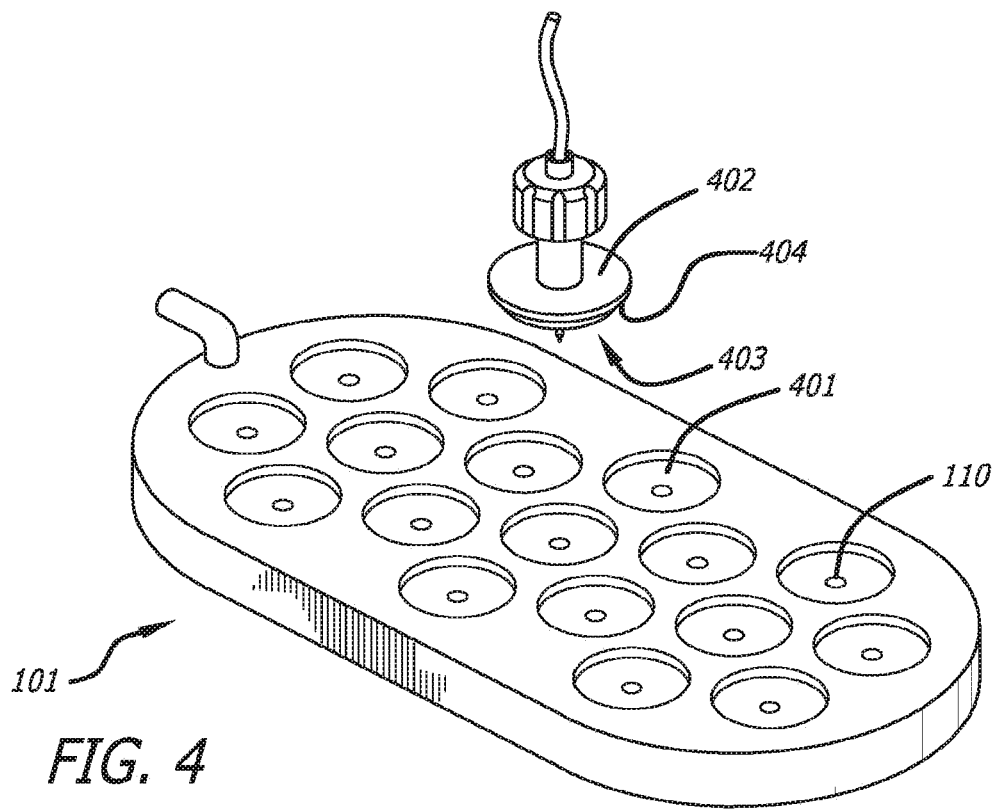
FIG. 4 depicts an embodiment of the platform including ports in the form of a blind-hole recess and the injection device including a stabilization disk.

Turning to FIG. 4, a further embodiment of platform 101 is depicted. In this embodiment, injection port 111 takes the form of an outer blind hole or cavity 401 formed in platform 101 and about through-hole 110. Injection device correspondingly includes as part of or affixed to a lower portion of housing 112 a disk 402 having a diameter sized larger than cavity 401. A bottom 403 of disk 402 further incorporates a shallow boss 404 that is sized slightly smaller than cavity 401 so that shallow boss may fit snugly within cavity 401 while the under portion 405 of the outer perimeter of disk 402 rests upon the top surface 406 about the injection port. This allows shallow boss 404 to fit snugly within cavity 401 while under portion 405 provides stability so as to achieve perpendicularity and concentricity of needle 108 to platform 101. Other embodiments might exclude a shallow boss and provide that the entire perimeter of disk 402 fit snuggly and securely within cavity 401 to achieve the same result. In the depicted embodiment, cavity 401 and disk 402 are circular, however, in other embodiments, they can be square, rectangular, ovoid, triangular, or any other shape that would provide sufficient support to meet the object of the invention.

In a yet further embodiment of platform 101, depicted by FIG. 5, each injection port 111 includes a notch 501 and the injection device includes a keyed protrusion 502. Notch 501 and keyed protrusion 502 are configured such that when base 113 of injection device 109 is inserted within injection port 109, notch 501 receives keyed protrusion 502 and causes housing 112 of injection device to remain rotatively fixed within injection port 111 at an interface point 503. In the depicted embodiment, a rotary mechanism 504 is supplied to automatically rotate needle 108 relative to housing 112. Turning briefly to FIG. 2A, mechanism 504 may be included as part of upper body 114 to turn interior lumen portion 215 relative to housing 112, with swivel fitting 214 providing rotational movement relative to tubing 117. The rotary mechanism 504 may include an electrically powered motor (e.g., a DC motor) or a mechanically powered (e.g., a wind-up spring). Mechanism 504 ensures a consistent rate of rotation in a direction 505 about through-hole 110 and in a plane parallel to top 103 of platform 101. Although not specifically shown, disk 402 and cavity 401 of the embodiment depicted by FIG. 4 may also include a similar notch and keyed protrusion, respectively, to accomplish the same or similar result.

The device allows for three-dimensional control of treatment solution delivery and dissection of subcutaneous tissues, not realized by present art. The platform typically controls a depth of between 4 mm and 20 mm below the surface of skin; however, a depth less than 4 mm or greater than 20 mm is contemplated. The cutting depth in a lateral direction 207 is controlled by various parameters, including the pressure of the fluid-jet at nozzle 209. The lateral cutting depth is measured orthogonally from the cutting tool, extending laterally between 4 mm and 25 mm. As the injection device is rotated, the pressure and other parameters may be varied to achieve different depths in lateral direction 207. Thus, the shape of the planar cut 302 in tissue 202 can vary. In some embodiments, the cut will be generally linear. In other embodiments, the cut may be ovoid. A circular cut 302 is depicted, however, with control and precision by the user of the injection device, it is conceived that substantially any shape may be achieved.

It is generally recognized that a large treatment site heals more slowly than a series of smaller treatment sites. Moreover, the larger the treatment site the greater the risk of skin necrosis and uneven healing, from which fibrosis may result. Turning to FIGS. 6A through 6C, this problem is addressed, by utilizing a number of injection ports having varied depths. In the embodiment of FIG. 6A, each injection port 111 includes a well 601 that limits the insertion depth of injection device 109. Each well 601 may have the same or different depth.

According to one embodiment of the invention the treatment sites are not continuous, meaning that there is no single continuous lesion. Each port 111 creates a different treatment site 302 as an island surrounded by tissue 202 which has not been treated (the fibrous septae have not been severed). After the tissue within a treatment site is treated, the injection device 109 is repositioned on an adjacent injection port 111 having a well 601 of a different depth. In some embodiments, the lateral cutting depth parameters are configured such that adjacent treatment sites 302 have zero spacing or overlap. In this manner, a site is treated and the process is repeated on the remaining desired sites at different depths, so that the resulting overall treatment is performed in a checkerboard fashion. A relatively large treatment area can thus be divided into a plurality of smaller treatment sites. Treatment at different depths (measured perpendicularly from the dermis) allows zero spacing (or overlapping) between adjacent sites, without creating a continuous lesion. As a result, the extent of untreated tissue can be greatly diminished, while minimizing the risks associated with large treatment sites. Thus, from a top view of platform 101 (e.g., FIG. 3) the plurality of treatment zones 302 appear to be continuous, however, referring briefly to FIG. 9, from a side view, it is clear that the "checkerboard" lesions 901 are at different treatment depths.

FIG. 6B depicts the embodiment of the injection device of FIG. 4 including stabilization disk 402 positioned at a different location on base 113 of needle housing 112. In this embodiment, needle 108 is a fixed length and base 113 may also be shortened or lengthened relative to needle 108. By varying the length of base 113 and the position of disk 402 a different insertion depth 203 of needle 108 is achieved. Housing 112 may be configured to adjust the length of base 113 by allowing base 113 to retract into upper body 114. In some embodiments, the device may include multiple injection devices 109 with varying needle lengths. In some embodiments, this may be accomplished by rotating upper body 114 relative to base 112 using grips 115. In other embodiments, base 113 may retract into upper body 114 against an opposing spring mechanism that includes a locking latch (not illustrated).

FIG. 6C depicts an embodiment of the injection ports of FIG. 5 including varying the length of notch 501 to vary the insertion depth of injection device 109 into a respective port 111. In this embodiment, needle 108 may be a fixed length, and when injection device 109 is inserted into port 111, the height of interface 503 along port 111 determines the depth of needle 108 into tissue 202.

The interspersing of treatment sites at different treatment depths is believed to accommodate rapid healing. More specifically, the interspersing of treatment sites at different treatment depths allows for closer spacing between treatment sites while accommodating for a more rapid healing response time of the injured tissue. A physician may also choose to vary the treatment depth based on the severity of the condition or specific body area.

As depicted by FIGS. 7A and 7B, in one embodiment a high-pressure syringe 701 can be used to supply a solution 702 to tubing 117. In this embodiment solution 702 is expelled from the syringe 701 by actuation of a syringe pump 703. A narrow channel 704 may be disposed at the distal end 705 of syringe 701. Tubing 117 is preferably connected to distal end 705 by any means known in the art. In some embodiments, channel 704 acts to increase the kinetic energy of solution 702 as it exits syringe 701 and moves into tubing 117. In further embodiments, syringe 701 may be used as a direct replacement for base 113 and/or upper body 114 of needle housing 112.

In yet further embodiments, as depicted by FIGS. 8A and 8B, the solution supply may include a rigid pressure canister 801 that encompasses a source of solution 802. Canister 801 includes a gas supply fitting 803 for filling canister 801 with a pressurized gas 804. Fitting allows canister 801 to be filled by compressed air or similar gas for pressurizing the closed space of canister 801. Canister 801 further includes a supply exit port 805 that is connectable to tubing 117 by any mean known in the art. Pressurized gas 804 acts on the source of solution 802 within canister 701 to move a pressurized solution 806 out of solution source 802 and out of supply exit port 805 connected to tubing 117. In the depicted embodiment, solution source 802 is a flexible bag containing sterile fluid that becomes pressurized by pressurized gas 804. Solution source 802 (a flexible bag in the depicted embodiment) may also include a supply tubing 807 for supply of solution 806. Supply tubing 807 may run through exit port 805 and connect directly to tubing 117 or, in some embodiments, may directly replace tubing 115 to connect directly to injection device 109.

The forgoing description for the preferred embodiments of the invention has been presented for the purposes of illustration and description. It is not intended to be exhaustive or to limit the invention to the precise form disclosed. Many modifications and variations are possible in light of the above teaching. It is intended that the scope of the invention not be limited by this detailed description, but by the claims and the equivalents to the claims appended hereto.

Although the present invention has been described in detail with regard to the preferred embodiments and drawings thereof, it should be apparent to those of ordinary skill in the art that various adaptations and modifications of the present invention may be accomplished without departing from the spirit and the scope of the invention. Accordingly, it is to be understood that the detailed description and the accompanying drawings as set forth hereinabove are not intended to limit the breadth of the present invention.

We claim:

1. A device for dissection of tissue, comprising:
a platform having a top surface, a bottom surface, and a downwardly extending wall about a perimeter of the platform,
wherein the bottom surface and the downwardly extending wall about the perimeter of the platform collectively form a recessed area in which a tissue to be dissected may be positioned;
the recessed area being operatively connected to a suction mechanism,
wherein the suction mechanism is configured to supply a suction force to the recessed area to allow the tissue to be dissected to be positioned against the bottom surface;
one or more ports positioned on top of the platform, each of the one or more ports positioned about a corresponding entry hole passing into the recessed area, wherein each of the one or more ports comprises a portion that is raised above the top surface of the platform that defines a corresponding well within a selected port and that limits an insertion depth of a needle or other cutting tool; and
the needle or other cutting tool comprising a base and an upper body,
wherein the needle or other cutting tool is configured to be removably secured to the platform,
wherein an outer perimeter of the base fits within an inner perimeter of a selected well,
wherein the upper body of the needle or other cutting tool is fluidically connected to a solution supply tubing, and
wherein the solution supply tubing is configured to deliver a solution to a lumen portion of the needle or other cutting tool,
wherein the needle or other cutting tool is configured to allow at least a portion of the needle or other cutting tool to be inserted into a selected port such that a distal end of the needle or other cutting tool passes through the corresponding entry hole into the recessed area, through a dermis and into a subcutaneous region of the tissue to be dissected positioned in contact with the bottom surface to a depth within the subcutaneous region,
wherein a lower portion of the upper body is configured to contact a portion of the corresponding well that is raised above the top surface of the platform when the distal end of the needle or other cutting tool is at the depth within the subcutaneous region, and
wherein the needle or other cutting tool dissects the tissue to be dissected in a plane below a surface of the tissue to be dissected in contact with the bottom surface.

2. The device of claim 1, wherein the depth within the subcutaneous region is between about 1 mm and 20 mm below the bottom surface, wherein the needle or other cutting tool comprises a needle, wherein the distal end of the needle or other cutting tool has one or more nozzles, wherein the one or more nozzles are configured to discharge a fluid in a direction orthogonal to a longitudinal axis of the needle and parallel to the top surface of the platform, and wherein the one or more nozzles are configured to increase a kinetic energy of the fluid discharged by the device through the needle.

3. A device of claim 1, wherein the suction mechanism comprises:
a vacuum fitting operably connected to the top surface of the platform and in fluid communication with the recessed area; and
a vacuum pump in fluid communication with the vacuum fitting.

4. The device of claim 1, further comprising a membrane formed of a flexible and resilient material applied to the bottom surface and across the corresponding entry hole, wherein the membrane is configured to minimize vacuum leakage through the corresponding entry hole.

5. A device for dissection of tissue, comprising:
a platform having a top surface, a bottom surface, and a downwardly extending wall about a perimeter of the platform,
wherein the bottom surface and the downwardly extending wall about the perimeter of the platform collectively form a recessed area in which a tissue to be dissected may be positioned;
the recessed area being operatively connected to a suction mechanism configured to supply a suction force to the recessed area to position the tissue to be dissected against the bottom surface;
one or more ports positioned on the platform, each of the one or more ports positioned about a corresponding entry hole in communication with the recessed area, wherein each of the one or more ports comprises a well; and
a needle or other cutting tool comprising a base, an upper body, and a swivel fitting positioned in the upper body,
wherein the swivel fitting comprises an upper and lower section, wherein the upper and lower sections are configured to rotate independently from one another, thereby allowing rotation of the needle or other cutting tool,
wherein the needle or other cutting tool is configured to be removably secured to the platform, wherein the needle or other cutting tool is configured to allow a portion of the needle or other cutting tool to be inserted into a selected port to pass a distal end of the needle or other cutting tool through the corresponding entry hole into the recessed area and into a subcutaneous region of the tissue to be dissected positioned in contact with the bottom surface to a depth a depth below a surface of the tissue to be dissected in contact with the bottom surface, and wherein each well comprises a raised portion that extends above the top surface of the platform and interacts with a rim on the upper body of the needle or other cutting tool and limits the insertion depth of the needle or other cutting tool.

6. The device of claim 5, wherein the needle or other cutting tool further comprises:

a needle comprising a distal end, the distal end having one or more nozzles, wherein the one or more nozzles are configured to discharge a solution in a direction substantially parallel to the top surface of the platform, wherein the one or more nozzles are configured to increase a kinetic energy of the solution discharged by the device through the needle.

7. The device of claim 5, further comprising a membrane formed of a flexible and resilient material applied to the bottom surface and across the corresponding entry holes, wherein the membrane is configured to minimize vacuum leakage through the corresponding entry holes.

8. The device of claim 5, wherein each entry hole comprises an inner indentation, wherein each inner indentation is larger than the corresponding entry hole.

9. The device of claim 8, wherein the inner indentation is configured to form a space for insertion of an individual membrane configured to minimize vacuum leakage through the entry hole.

10. The device of claim 5, wherein, the rim on the upper body is on a lower portion of the upper body and is formed as a result of an outer dimension of the upper body being greater than a corresponding outer dimension of the base.

11. The device of claim 5, wherein each well has the same depth.

* * * * *